United States Patent
Szlema et al.

[11] Patent Number: 6,149,616
[45] Date of Patent: Nov. 21, 2000

[54] BANDAGE FOR THE KNEE JOINT

[75] Inventors: Ingeborg Szlema, Kempen; Dieter Brandt, Düsseldorf, both of Germany

[73] Assignee: Beiersdorf Aktiengesellschaft, Hamburg, Germany

[21] Appl. No.: 08/615,583

[22] Filed: Mar. 12, 1996

Related U.S. Application Data

[63] Continuation of application No. 08/145,823, Nov. 2, 1993.

[30] Foreign Application Priority Data

| Nov. 5, 1992 | [DE] | Germany | 42 37 389 |
| Aug. 4, 1993 | [EP] | European Pat. Off. | 93112490 |

[51] Int. Cl.[7] ..................................... A61F 13/00
[52] U.S. Cl. .................. 602/62; 602/63; 602/26
[58] Field of Search .................. 602/26, 60–64; 606/204; 128/852

[56] References Cited

U.S. PATENT DOCUMENTS

| 3,375,821 | 4/1968 | Meek | 602/26 |
| 3,831,467 | 8/1974 | Moore | 602/62 |
| 4,116,236 | 9/1978 | Albert | 602/26 |
| 4,287,885 | 9/1981 | Applegate . | |
| 4,425,912 | 1/1984 | Harper | 602/26 |
| 4,445,505 | 5/1984 | Labour et al. | 602/26 |
| 4,986,263 | 1/1991 | Dickerson . | |
| 5,135,473 | 8/1992 | Epler et al. | 602/62 |
| 5,185,000 | 2/1993 | Brandt et al. | 602/63 |
| 5,261,871 | 11/1993 | Greenfield | 602/62 |
| 5,306,229 | 4/1994 | Brandt et al. | 602/56 |

FOREIGN PATENT DOCUMENTS

| 0154758 | 9/1985 | European Pat. Off. . | |
| 0496071 | 7/1992 | European Pat. Off. . | |
| 0498062 | 8/1992 | European Pat. Off. . | |
| 2607384 | 3/1988 | France . | |
| 2607384 | 6/1988 | France . | |
| 2633512 | 1/1990 | France | 602/63 |
| 2636228 | 11/1990 | France . | |
| 1015364 | 9/1957 | Germany | 2/239 |
| 2632706 | 1/1978 | Germany | 602/63 |
| 2936174 | 3/1981 | Germany | 602/63 |
| 3416231 | 11/1985 | Germany . | |
| 3637879 | 5/1988 | Germany | 602/63 |
| 9004974 | 9/1990 | Germany . | |
| 3991334 | 7/1992 | Germany . | |
| 4103383 | 8/1992 | Germany | 602/63 |
| 4238610 | 5/1994 | Germany | 602/26 |
| 8504569 | 10/1985 | WIPO . | |

*Primary Examiner*—Mickey Yu
*Assistant Examiner*—Denise Pothier
*Attorney, Agent, or Firm*—Friedrich Kueffner

[57] ABSTRACT

The bandage (10) for overload symptoms, femoropatellar pain syndromes and the patella point syndrome of an elastic bandage cloth in tubular form with a circumferentially extending insert (30) of a wavy knitted fabric (40) posesses in the front bandage portion (12) a pressure pad (50) or an annular pressure pad located within the area above the patella when the bandage is applied, which is open towards the top and leaves the quadriceps tenson uncovered (FIG. 1).

44 Claims, 17 Drawing Sheets

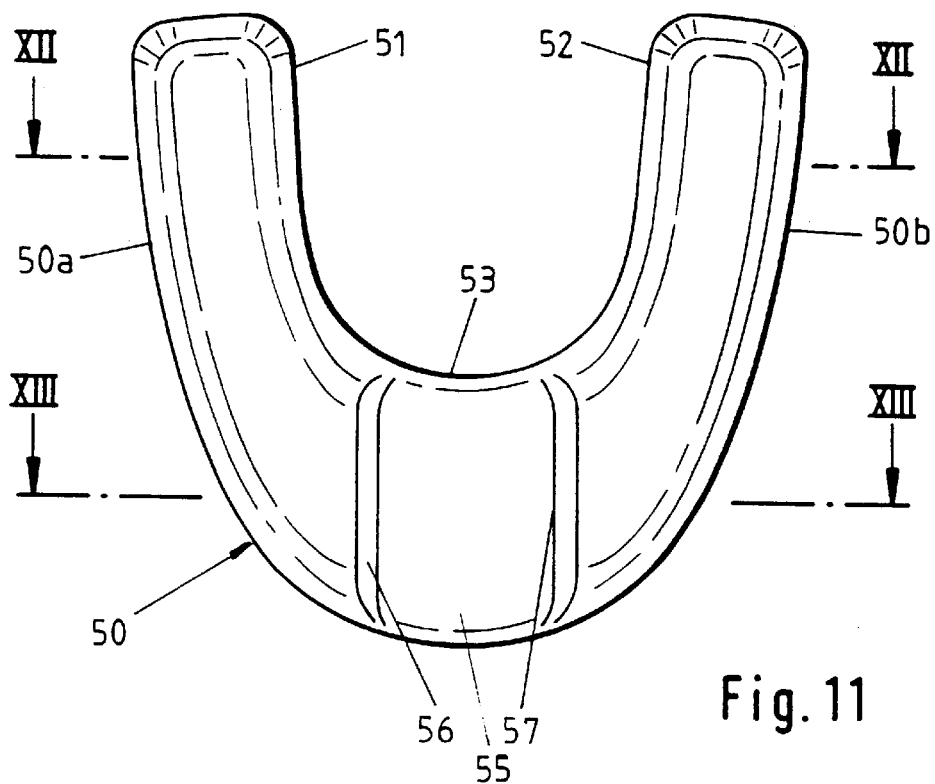
Fig. 11
Fig. 12
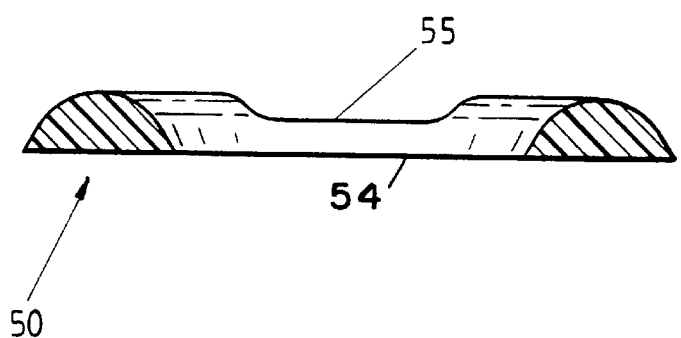
Fig. 13
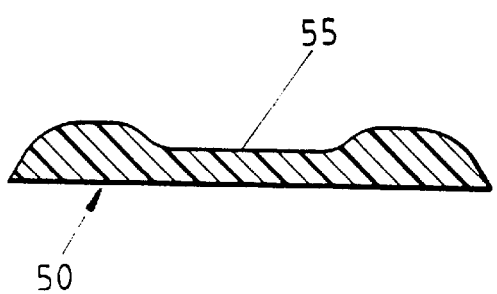

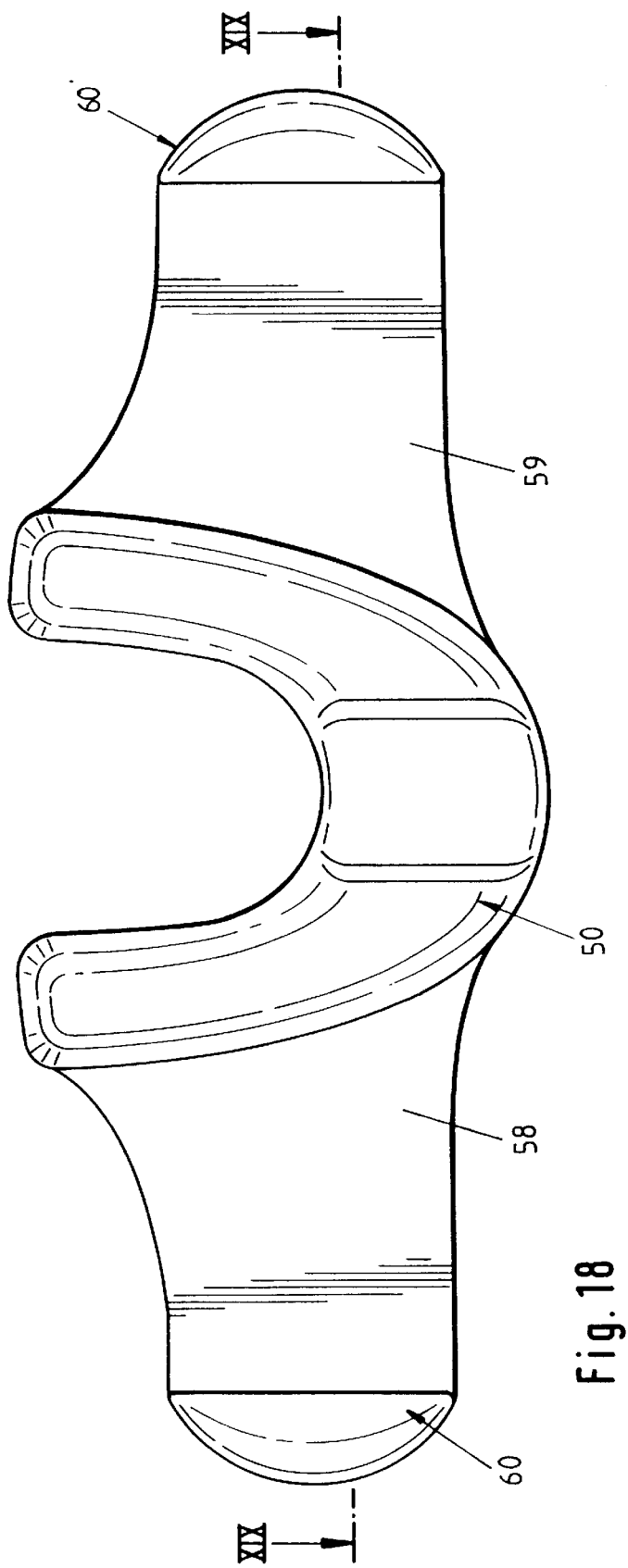
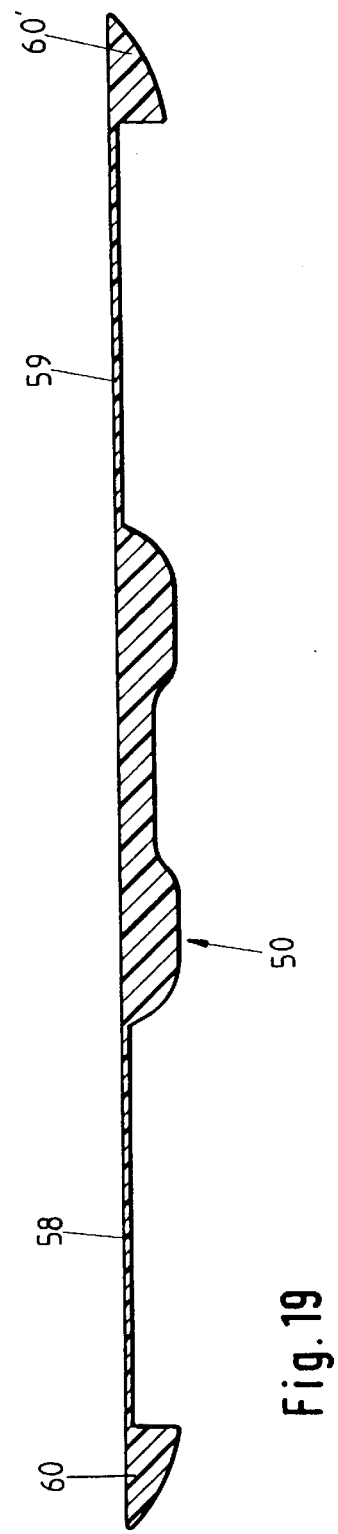
Fig. 18
Fig. 19

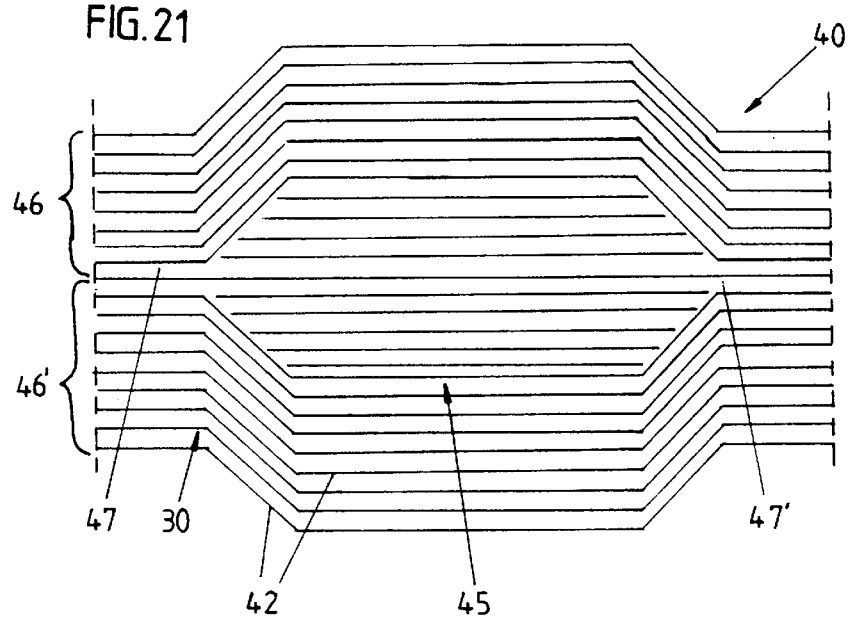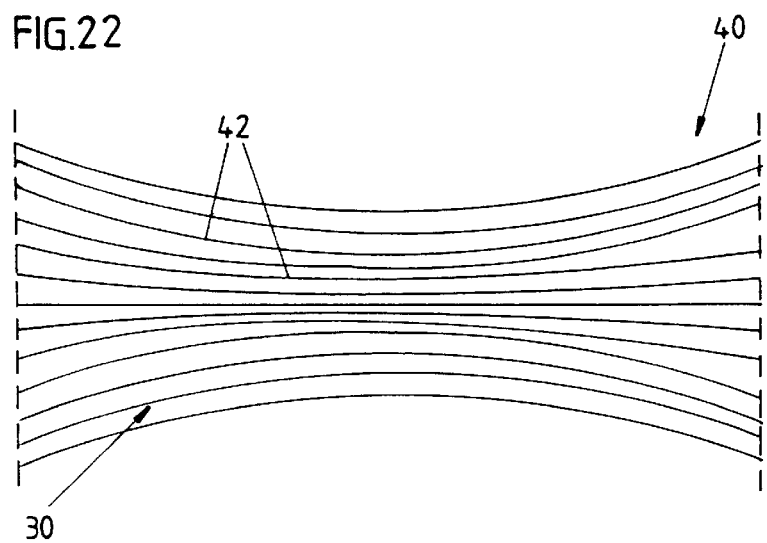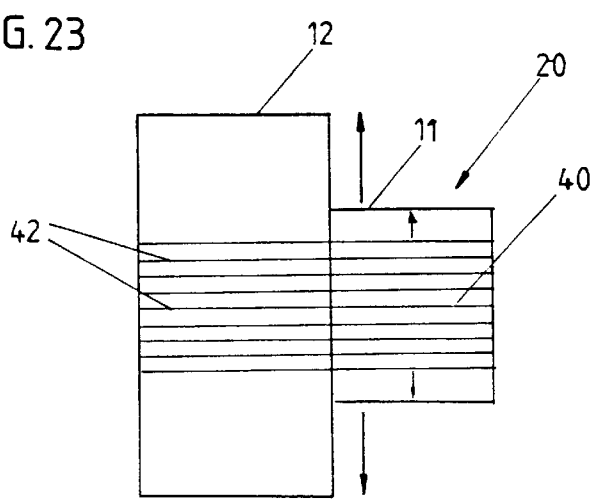

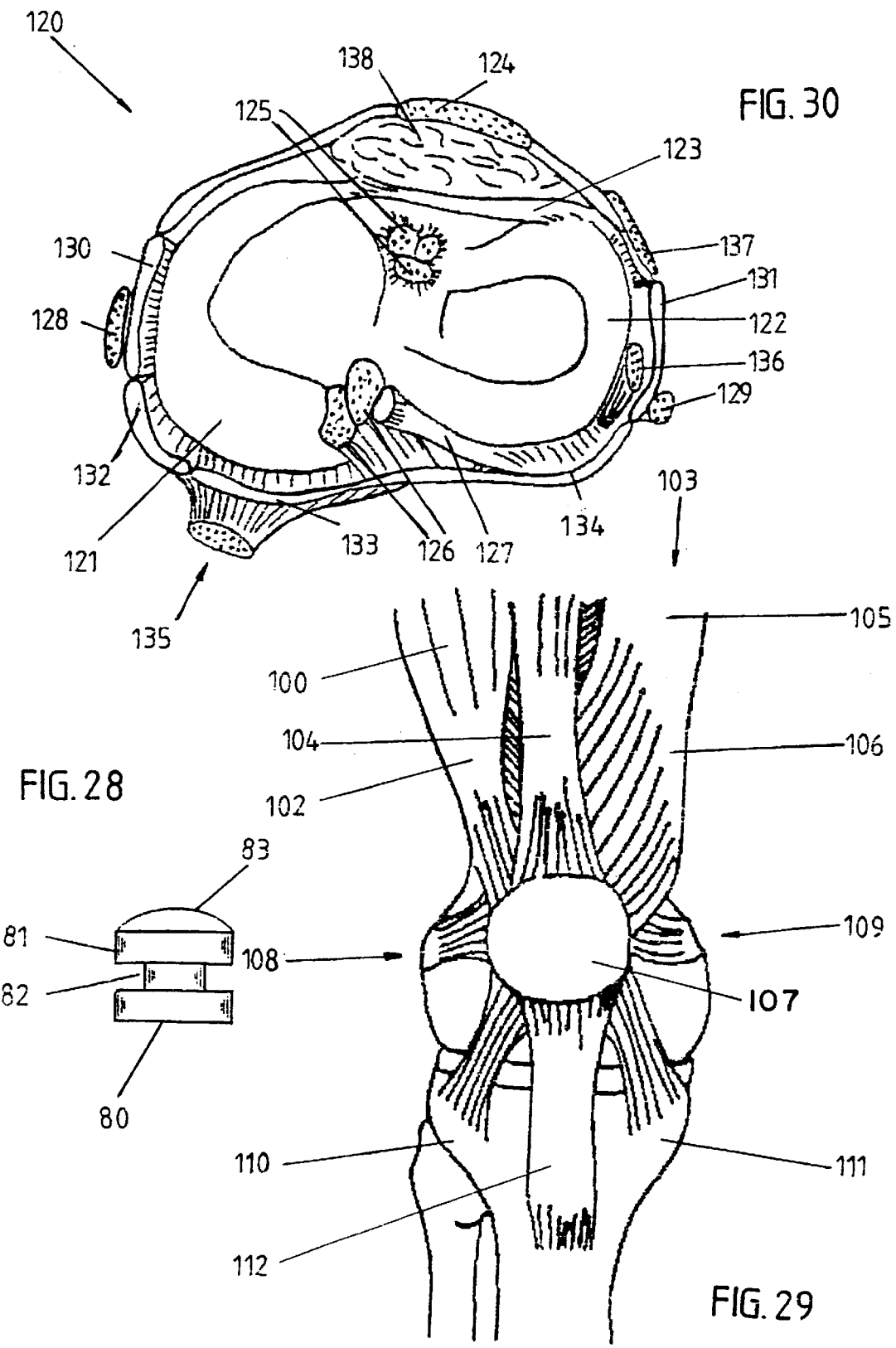

BANDAGE FOR THE KNEE JOINT

This is a continuation of application Ser. No. 08/145,823 filed Nov. 2, 1993.

BACKGROUND OF THE INVENTION

The present invention relates to a bandage for the knee joint of elastic bandage cloth in tubular form having a front bandage portion and a rearward bandage portion and at least one longitudinally extending spring rod.

The knee is the most injury-prone joint of the body and, at the same time, the joint which is most frequently affected by arthroses since it is instable and bears the full weight of the body. Muscular imbalances are also frequently the reason for pains in the anterior knee cap. Particularly in persons who pursue sedentary professions, the ischiocrural musculature is for the most part contracted and draws the articular capsule to the rear, whereby the contact pressure is increased in an unphysiological fashion. Sporting injuries of the knee joint result above all when football is played and when skiing by a sudden twisting of the lower leg and due to the weight being placed on the same. Lesions of the knee mostly result in local pain. The complexity of the joint renders the exact diagnosis difficult. That is why it frequently happens that patients fail to receive the correct initial treatment which may lead to degenerative diseases later on.

For the medical care of injuries to the knee, a great variety of therapeutic aids for the immobilization or the restricted movement as well as for supporting and relieving the knee joint are available. Also a wealth of products supply the area of active bandages, as are not available in such a wide range for any other part of the body. Thus, from the DE-A 34 16 231, a knee bandage for being slipped on of elastic material with, if necessary, sewn-in longitudinally proceeding springs for reinforcing the medial and lateral side of the knee joint, a recess for the patella and a padding surrounding the recess is known, in which case the padding which surrounds the recess is constructed in such a way that a contact pressure on the patellar ligament results which relieves the femoropatellar gliding surface. On this occasion the padding surrounds the recess in a U-shaped manner, the U shape being open in the upward direction. The padding constitutes an elastic U-shaped element sewn into the knee joint bandage which surrounds the recess solely laterally and from below. This element is comprised of silicon material or of rubber. In addition, the U-shaped element is constructed in the form of a bead facing the body with its convex side. However, what is essential in this knee joint bandage is that the main volume of the padding or of the bead is disposed above the patellar ligament. Apart from a pleasant wearing sensation it is intended to achieve an optimal relief of the knee joint while the same is guided at the same time so as to ensure an as short as possible and gentle recovery in the case of injuries, irritations or other pathological conditions. However, no pressure relief on the patellar ligament is provided by this knee joint bandage for it is after all a contact pressure which is intended to be achieved onto the patellar ligament. The knee joint bandage according to the DE-U 90 04 974 comprises a downwardly conically tapering knee stocking of an elastic material, such as a rubber fabric. On its front side, within the region of the patella, the knee stocking carries two mounting means extending downwardly from the top which support the patella laterally while the same rests on their underside. This knee joint bandage is intended to permit a vertical change of the patella relative to the muscles, but to retain the patella vis-à-vis the gliding surface in the raised state by supporting the patella from below.

The DE-A 39 91 334 describes an elastic knee joint bandage in tubular form having an elastic shaped insert embracing the patella in a recess. Into the shaped insert, firmly connected with the same, a flexible, non-extensible tightening member is embedded which connects the regions of the shaped insert adjacent to the patellar poles in the fibular side in an arc around the patella in such a way that, when the distance of these regions is increased when the knee joint is flexed, the distance of the arc from the connection line of the patellar poles is decreased and the border in question of the recess of the shaped insert presses onto the adjacent side of the patella while medially displacing and centering the same. With this knee bandage it is intended to dynamically influence a patella which, from its ideal position, is displaced on the fibular side either pathologically or in the form of a very frequent variant from the norm during the flexion of the knee joint in order to correct the patellar position in the process. However, when the knee joint is flexed, the clasp used in this knee joint bandage is pulled apart with the result that the clasp straightens out and the desired centering effect is not fully achieved.

The invention is based upon the technical problem of providing a bandage for the knee joint, hereinafter referred to as genu knee joint bandage and knee joint bandages based upon the same hereinafter referred to as patella knee joint bandage to be employed where a lateralization tendency of the patella exists, with the aid of which the following is intended to be achieved.

Support of the physiotherapy. An important component of the physiotherapeutical treatment being the stretching of the ischiocrural muscles.

Relief of the knee joint and the patella.

Bringing about a speedy detumescence, alleviation of pain and functional improvement.

Performing an intermittent compression and massage on the articular soft tissue.

Avoiding an undesirable pressure on the patella and the cartilaginous layer located therebeneath.

Reduction of the contact pressure on the patella.

Maintenance of the physiological gliding ability of the patella.

Relieving the attachment of the ischiocrural muscles.

Avoiding an undesirable pressure on the nerves and blood vessels which run in the hollow of the knee.

Avoiding negative effects on the muscular activity.

Avoiding a creasing of the bandage in the hollow of the knee.

No impairment of the function of the quadriceps tendon of pulling the patella into its correct position, In this connection, the patella knee joint bandage is, over and above that, intended to possess the following properties:

lateral guidance of the patella for reducing the lateral deviation.

SUMMARY OF THE INVENTION

This technical problem is resolved in a bandage for knee joints with the aid of the following features.

According to an embodiment of the invention, a genu knee joint bandage is comprised of an anatomically configured tubular body of a woven fabric or knitted fabric having a circumferentially extending high-elasticity wavy knitted fabric, in which case, with the aid of seams interconnecting the rearward bandage portion with the front bandage portion, spring rods are incorporated into the tubular body material. in the front bandage portion, a first pressure pad of a soft or soft-elastic material is disposed located above the patella when the bandage is applied, which leaves the quadriceps tendon uncovered. According to further embodiments, a second or a second and a third pressure pad of a soft or soft-elastic material which acts upon the ischiocrural musculature is inserted into the rearward bandage portion. Apart from a pressure pad constructed in a U-shaped manner, it is also possible to employ an annular pressure pad of a soft or soft-elastic material.

The patella knee joint bandage according to another embodiment, in its front bandage portion, is additionally provided with at least one clasp which stabilizes the first pressure pad and extends in the bandage longitudinal direction, which is an integrated component of the first pressure pad or which is located laterally relative to the same. This clasp is elastic and, by preference, elastic in the longitudinal direction.

With a thusly contructed bandage for the knee joint it is possible to effectively treat the following indications on the knee:

Irritations and overload phenomena of the knee joint.

Distorsions and contusions.

Articular effusions and tumefactions in arthrosis and arthritis.

Myotenopathies.

Weakness of the ligaments.

Patellar point syndrome.

Dislocation tendency of the patella.

lateralization tendency of the patella.

Patellar chondropathy.

The indication frame "painful irritations of the knee joint" is very broadly formulated and extends from soft tissue tumescences following sporting accidents or accidents at work via chronic complaints to femoropatellar displasias with lateralization tendency. The latter call for constructional features in a knee joint bandage which go beyond the properties necessary for the therapy of general knee complaints. To incorporate all power factors into a product would have restrictive repercussions on the indication area: The bandage becomes a special bandage and would e.g. constitute an excessive medical care in the case of unspecific knee pains. That is why it is advantageous for two bandages to be employed, viz. the genu knee joint bandage as a general basic product for excessive straining phenomena, femoropatellar pain syndromes and for the patellar point syndrome, whereas the patella knee joint bandage represents the product based upon this genu knee joint bandage and is employed in cases of lateralization tendency and chondropathic complaints. Both bandages, the genu knee joint bandage and the patella knee joint bandage, are based upon each other.

That is why the action-related characteristics and advantages of both bandages are very largely identical while, for the patella knee joint bandage, still further advantages are added. With the aid of the genu and patella bandages, the physiotherapy is assisted and the knee joint and the patella are relieved. A speedy detumescence, alleviation of pain and functional improvement are brought about. Over and above that, an intermittent compression is exerted on the soft tissues and a deep-acting massage is effected. An undesirable pressure on the patella and the cartilaginous covering located therebeneath is avoided. The contact pressure of the patella is reduced while its physiological gliding ability is maintained. The attachment of the ischiocrural muscles is relieved. An undesirable pressure on the nerves and blood vessels which run in the hollow of the knee is avoided. No negative repercussions result on the muscular activity. The bandage is not too tight and does not cause any circulatory difficulties. A creasing of the bandage in the hollow of the knee during a flexion of the knee is minimized. The bandage does not slip and a continuous good seating is retained even when moving. With the bandage, a high degree of wearing comfort is achieved since it does not chafe and is kind to the skin. Moreover, the knee joint bandage has the advantage that the function of the quadriceps tendon of pulling the patella into its correct position is not impaired. In addition, in the patella knee joint bandage, a lateral guidance of the patella is effected, whereby the lateral deviation is reduced.

The genu knee joint bandage is a three-dimensional anatomical two-stretch bandage which is knitted to shape which extends from the lower leg to the thigh and possesses a functional slight flexural position of approximately 10° and is fitted with pressure-reducing borders. The bandage itself is comprised of two portions, in which case the front bandage portion embraces two thirds of the leg circumference. Above the knee joint, an insert of highly elastic wavy knitted fabric is located. The rearward bandage portion is sewn in with the pretensioned wave of the wavy knitted fabric.

Spring rods sewn into pockets above the lateral seams keep the bandage tensioned. Above the patella, the wavy knitted fabric is closed. Within the region above the patella, a preferably horseshoe-like constructed first pressure pad is to be found. The upwardly open pressure pad leaves the quadriceps tendon uncovered. In the lower part, the contour of the pressure pad is adapted to the tibial condyle and the course of the patellar ligament. This pressure pad disposed in the front bandage portion preferably contains a button-shaped friction core of a material which, in comparison with the material of the pressure pad, possesses a higher degree of hardness. Said friction core is disposed so as to be infrapatellar. Into the rearward bandage portion, a pressure pad or two pressure pads is/are sewn in which is/are constructed in an elliptic fashion or which possess other configurations and which act upon the attachment of the ischiocrural musculature. These two pressure pads are located approximately 1 cm above the knee joint cavity immediately at the lateral seams, with the aid of which the front bandage portion is connected with the rearward bandage portion.

The patella knee joint bandage, too, is a three-dimensional anatomical two-stretch bandage knitted to shape for the knee joint. The bandage extends from the lower leg to the thigh and possesses a functional slight flexural position of approximately 10° and is fitted with pressure-reducing borders. The bandage is likewise comprised of two portions, in which case the front portion embraces two thirds of the leg circumference. Above the knee joint, an insert extending around the entire leg of a high-elasticity wavy knitted fabric is located. The rearward bandage portion is sewn in with the wave in a pretensioned state. Spring rods incorporated with the aid of the lateral seams keep the bandage taut. The knitted fabric is closed above the patella. Within the region above the patella, a first, preferably horseshoe-like constructed pressure pad is to be found. The pressure pad which is open toward the top leaves the quadriceps tendon uncovered. In the lower part, the contour of the pressure pad is adapted to the tibial condyle and to the course of the patellar ligament. The pressure pad employed in the patella bandage may comprise a button-like friction core which is comprised of a material whose degree of hardness is higher than the degree of hardness of the material from which the pressure pad is fabricated. This friction core is in this case disposed so as to be infrapatellar. In addition, the pressure pad of the patella knee joint bandage can be provided with a component that possesses different stretching properties. The first pressure pad is laterally connected with a fan-shaped strip or with a clasp, which preferably is comprised of a springable elastic material, but which possesses no longitudinal elasticity. When, during the movement between stretching and flexion, an extension of the elastic elements in the bandage takes place, this strip or the clasp pulls itself straight and exerts a centering force on the pressure pad. Two elliptic pressure pads can be sewn into the rearward bandage portion of the patella knee joint bandage, which act upon the attachment of the ischiocrural musculature. These two pressure pads are located approximately 1 cm above the knee joint cavity immediately next to the lateral seams.

Especially advantageous is the arrangement of the wavy knitted fabric of which the insert is comprised which is disposed within the area of flexion of the bandage. This wavy knitted fabric possesses, on at least one side, a relief in the form of a wavy structure. This wavy structure is elastically pretensioned and stabilized by a subjacent thread arrangement of higher elastic yarn or threads, whereby the covering structure, in the relieved state of the wavy knitted fabric, bulges out in a wave-like, by preference, in a half-wave fashion. When this fabric is accordingly employed in a bandage and strained vertically for the alignment of the transverse waves which, by way of example, is the case when the bandaged joint is flexed, in that case, to begin with, merely the transverse waves are pulled so as to become flatter or smooth without a stretching or straining of the covering structure taking place. In this manner it is possible to reliably rule out an overstretching of the covering structure, whereby, at the same time, the occurrence of creases, and this even after a prolonged wearing of the bandage, is avoided in the internally located joint flexion region. That is why the wavy knitted fabric is particularly well suited for use in bandages that are made use of for those joints which possess a large free space for movement or angle of flexion as is e.g. the case in knee joint bandages. In this connection the construction is especially advantageous, according to which the wavy knitted fabric possesses a wavy structure of a covering structure formed at least on one side and substantially vertically aligned to the main direction of elongation, in which case this wavy structure is elastically pretensioned and stabilized by an incorporated thread arrangement which may also be subjacent to said covering structure, which is connected with the covering structure at predetermined intervals and is configured in such a way that the number of the transverse waves is greatest where, due to the flexion of the joint, the largest elongation path occurs.

Such a wavy knitted fabric thus permits, in spite of a relatively high extensibility, the use of relatively inelastic yarn for the covering structure, whereby the prerequisite for an economic production of the wavy knitted fabric is provided. Moreover, in the wavy knitted fabric no risk exists of the used yarn being overstretched since a great basic elasticity exists.

BRIEF DESCRIPTION OF THE DRAWINGS

Embodiment examples of the invention are explained in greater detail below with the aid of the drawings. In the drawing

FIG. 11 shows, in a view from the front, the U-shaped pressure pad;

FIG. 12 shows a vertical section in the direction of line XII—XII in FIG. 11;

FIG. 13 shows a vertical section in the direction of line XIII—XIII in FIG. 11;

FIG. 18 shows, in a view from the front, a U-shaped pressure pad with lateral elliptic pressure pads connected with the pressure pad by means of webs;

FIG. 19 shows a vertical section in the direction of line XIX—XIX in FIG. 18;

FIG. 21 shows, in a schematic view from the front, an insert disposed so as to extend circumferentially in the bandage which is comprised of a highly elastic wavy knitted fabric;

FIG. 22 shows, in a view from the rear, the insert of the high elasticity wavy knitted fabric;

FIG. 23 shows, in a schematic representation, the construction of the high-elasticity wavy knitted fabric in the front bandage portion and in the rearward bandage portion of the knee joint bandage;

FIG. 28 shows, in a side view, a friction core disposed in the U-shaped pressure pad;

FIG. 29 shows a view onto the human knee joint;

FIG. 30 shows the right tibia in a cross-section;

DETAILED DESCRIPTION OF THE PREFERRED EMBODIMENT

Figure 1:
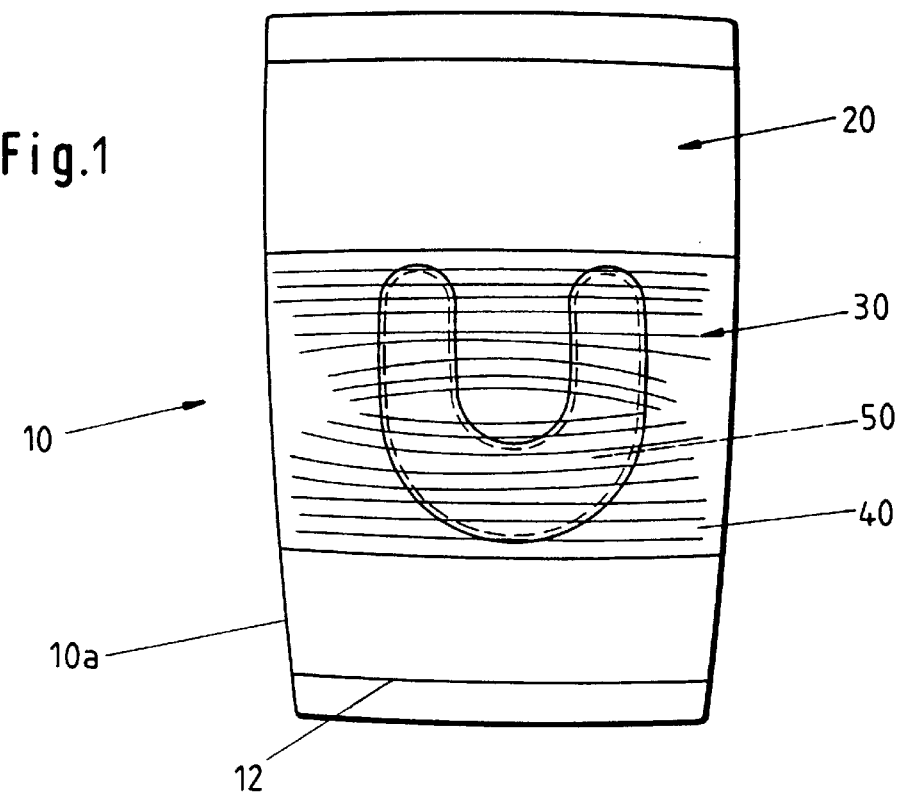
FIG. 1 shows, in a view from the top, a genu knee joint bandage with a U-shaped pressure pad provided with spring rods disposed in the rearward bandage portion of the same and two elliptic pressure pads.

The knee joint reproduced in FIG. 29 located in the center of the movement chain "lower extremity" is the largest joint of the human body. The upper joint corpus is a roll which is notched in the center. It is faced only by a very flat joint surface formed by the tibia. The menisci, two cartilaginous plates lying on the tibial joint surface constitute the sockets in which the roll of the upper joint corpus is able to move in a hinge-like fashion. An osseous guide for the knee does not exist. This function is taken over by other structures. The strong lateral ligaments serve as guide rails for the hingelike motion. The slipping through of the bones forming the joint toward the rear or to the front is prevented by the short cruciate knee ligaments located in the interior of the joint. In front of the joint, embedded in a tendon, the patella is located. It is the largest free bone and serves to improve the tractional effect of the lower leg extensor muscle. The patellar tendon is highly sensitive.

In the knee joint depicted in FIG. 29, the musculus vastus lateralis is identified with 100, the tendo musculi vasti with 102, the musculus vastus intermedius with 103, the musculus vastus recto femoris with 104, the musculus vastus medialis with 105, the musculus vastus medialis obliquus with 106, the patella with 107, the ligamentum patellofemorale laterale with 108, the ligamentum patellofemorale mediale with 109, the ligamentum patellotibiale laterale with 110, the ligamentum patellotibiale mediale with 111 and the ligamentum patellae with 112.

The stabilizers of the knee joint are in this case divided into four functional units. The stabilizers of the medial and lateral complex as well as the dorsal and ventral structures, in which case a distinction is made between static and dynamic stabilizers.

The FIG. 30 shows the right tibia 120 in across-section. Here, the internal or medial meniscus is identified with 121, the external or lateral meniscus with 122, the ligamentum genus transversum with 123, the ligamentum patellae with 124, the ligamentum cruciatum anterius with 125, the ligamentum cruciatum posterius with 126, the ligamentum meniscofemorale posterius with 127, the ligamentum collaterale mediale with 128, the ligamentum collaterale laterale with 129, the medial capsular ligament with 130, the lateral capsular ligament with 131, the ligamentum obliquuum posterius with 132, the ligamentum politeum obliuum with 133, the ligamentum popliteum arcuatum with 134, the musculus semimembranosus with 135, the musculus popliteus with 136, the tractus iliotibialis with 137 and Hoffa's fat pad with 138.

The bandage 10 for a knee joint illustrated in the drawing comprises an anatomically configured tubular body 20 of a woven or a knitted fabric with an insert 30 extending circumferentially through said bandage of a high-elasticity wavy knitted fabric 40. Via the seams which interconnect the rearward bandage portion 11 with the front bandage portion 12, flat spring rods 13,14 are sewn into the tubular body material which, in accordance with the anatomical configuration of the tubular body 20, are constructed so as to be proceeding in an arcuate fashion, as is shown in the FIGS. 2 and 4. These spring rods 13,14 are constructed so as to proceed in a straight manner; they will be imparted the arcuate shape only afterwards when the bandage is constructed.

In the front bandage portion 12 of the bandage 10, a first upwardly open pressure pad 50 leaving the quadriceps tendon uncovered of a soft or soft-elastic material is disposed, in which case this pressure pad 50 is seated about the patella when the bandage is applied. This pressure pad 50 is constructed so as to be U-shaped and is formed by the legs 51,52 and the web 53 interconnecting the legs; it being also possible for the pressure pad 50 to be constructed in a V-shaped manner. Into the rearward bandage portion 11 of the bandage 10, a second or a second and third pressure pad 60,60' is/are inserted which acts/act upon the attachment of the ischiocrural musculature, which is likewise comprised of a soft or soft-elastic material.

Figure 2:
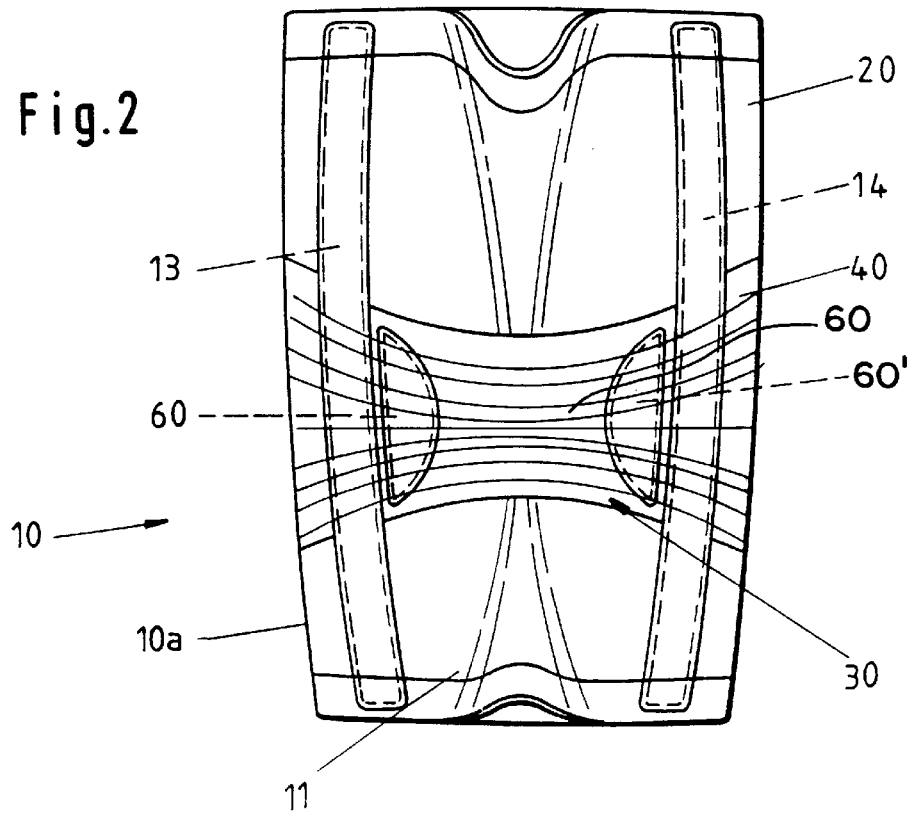
FIG. 2 shows a rear view of the genu knee joint bandage.

FIGS. 1 and 2 show a bandage 10 which is constructed in the form of a genu knee joint bandage 10*a*.

Figure 3:
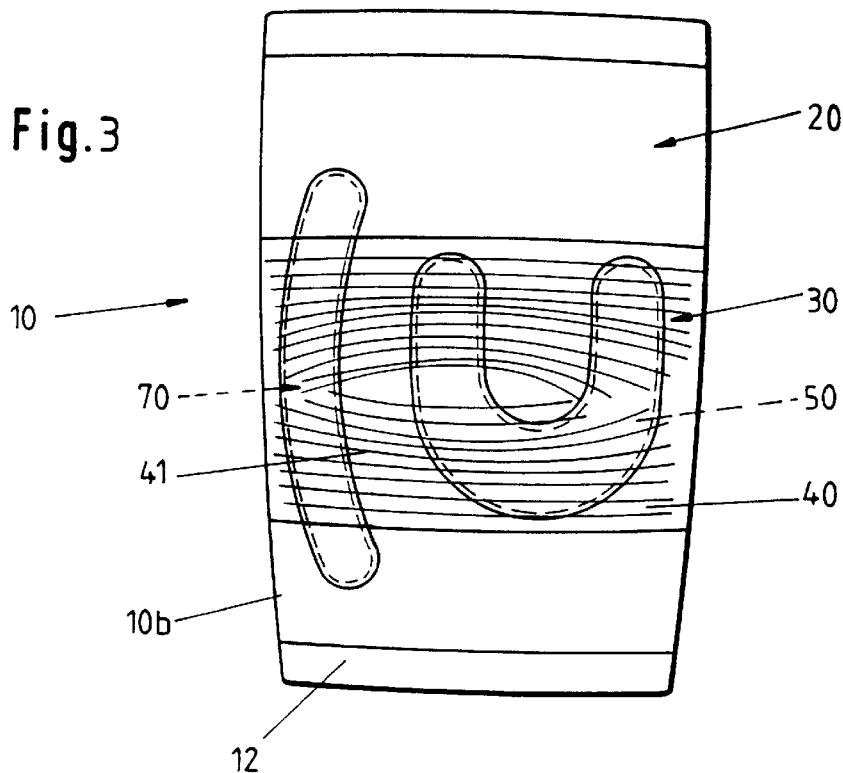
FIG. 3 shows, in a view from the front, a patella knee joint bandage with a U-shaped pressure pad and with a pressure pad centering clasp laterally disposed at a distance from the same and with spring bars disposed in the rearward bandage portion and two elliptic pressure pads.
Figure 4:
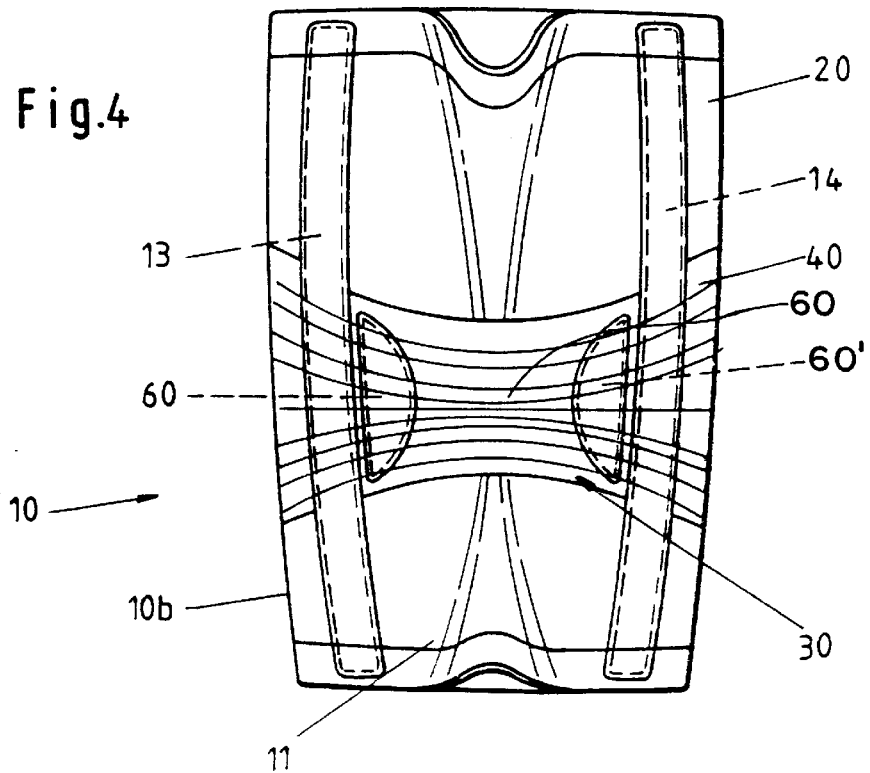
FIG. 4 shows a rear view of the patella knee joint bandage.

As a further embodiment of the bandage 10, according to FIGS. 3 and 4, a patella knee joint bandage 10*b* is provided which is based upon the genu knee joint bandage, which differs from the genu knee joint bandage 10*a* solely in that, in the front bandage portion 12, at least one elastic clasp 70 is additionally disposed which stabilizes the pressure pad 50 and proceeds in the longitudinal direction of the bandage, in which case this clasp is an integral component of the pressure pad 50 or is located laterally to the same. This clasp 70 does preferably not possess any longitudinal elasticity.

Figure 7:
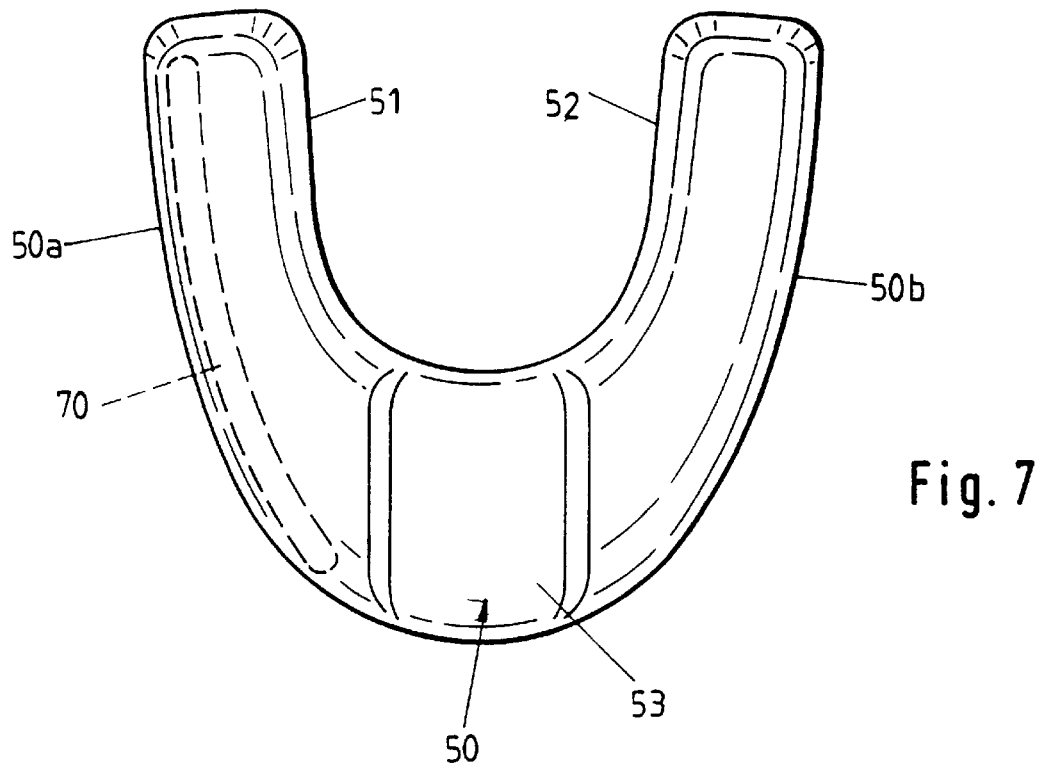
FIG. 7 shows, in a view from the front, the U-shaped pressure pad with a pressure pad centering clasp integrated into one of the pressure pad legs of the same.
Figure 10:
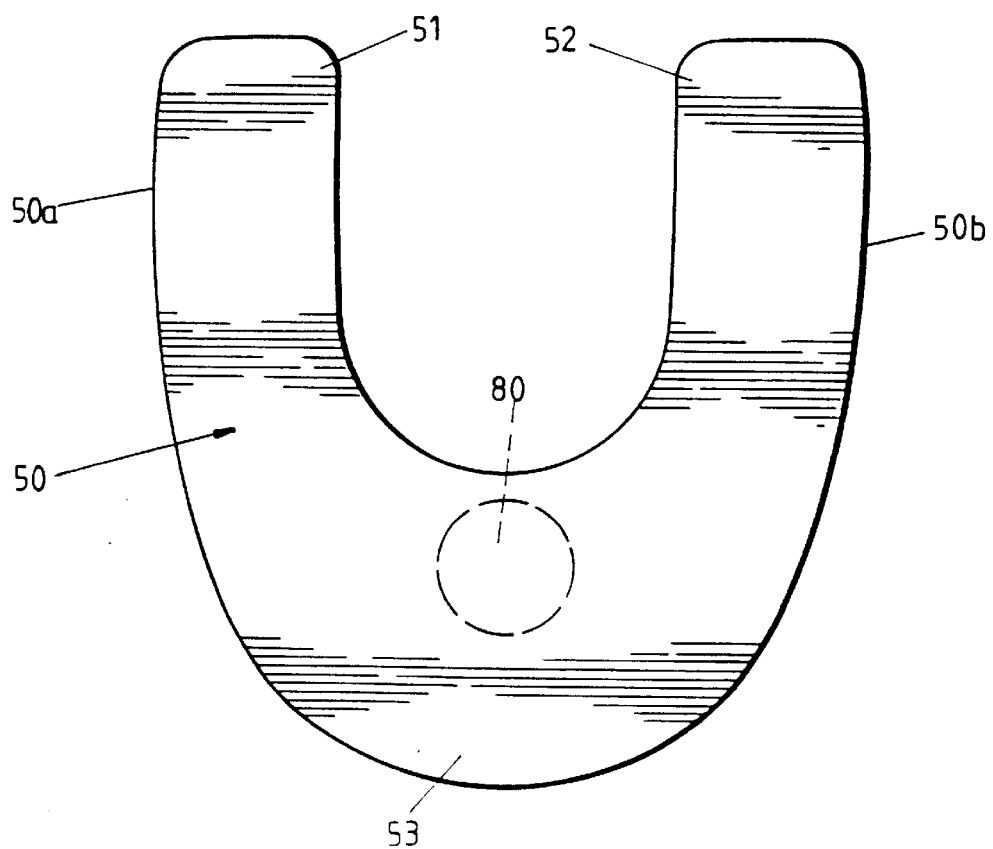
FIG. 10 shows, in a view from the front, a U-shaped pressure pad provided with a friction core.
Figure 14:
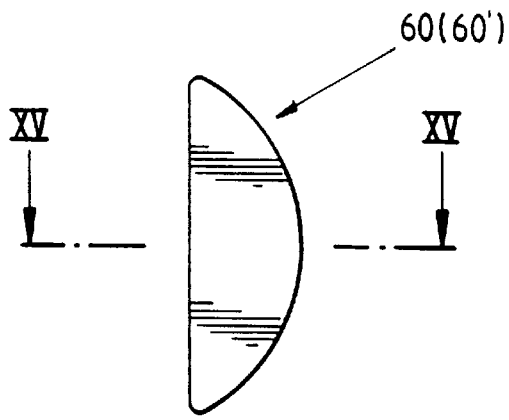
FIG. 14 shows, in a view from the front, an elliptic pressure pad.
Figure 15:
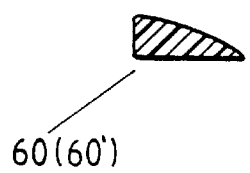
FIG. 15 shows a vertical section in the direction of line XV—XV in FIG. 14.

According to a first embodiment, the pressure pad 50 in the front bandage portion 12 has a horseshoe-like configuration with an arcuate course of the outer borders 50*a*,50*b* of the two pressure pad legs 51,52 (FIGS. 7, 10 and 11). The pressure pad 50 is provided with an externally located even surface area 54 the cross-section of the pressure pad legs 51,52 and the cross-section in a subsection of the pressure pad web 53 corresponds to a semicircle waves 42 while the wavy knitted fabric in the front bandage portion 12 is simultaneously contracted (FIG. 23). A peculiarity of the bandage 10 consists in that, for the insert 30 which is provided where the greatest alternating elongation stresses of the bandage occur, a special textile structure is employed, viz. The wavy knitted fabric 40, which will be explained in greater detail hereinafter. However, the possibility also exists of letting the waves 42 of the wavy knitted fabric 40 of the insert 30 in the front bandage portion 12 proceed linearly and parallelly. The lateral guides 56,57 serve to guide the patellar ligament. It is essential, however, that this recess 55 in the pressure pad 50 not only results in a pressure reduction but that it is also adapted to the contour of the tendon.

The pressure pad 50 comprises felt, sponge rubber, neoprene, rubber, a viscoelastic silicone rubber or an elastic, compressible, pressure-deformable silicone rubber or a material which possesses the same elasticity properties, such as natural rubber, foamed silicone or such like.

The pressure pad 50 can also be constructed in the form of a bag or pouch and be provided with a filling of a gaseous or liquid medium.

Figure 5:
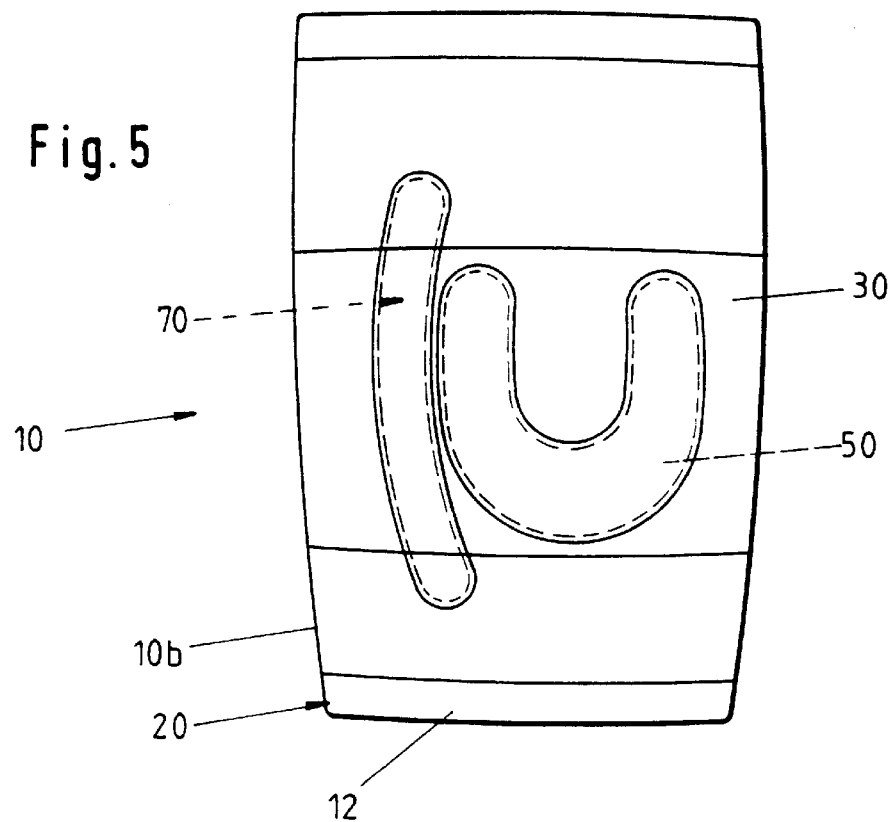
FIG. 5 shows, in a view from the front, a further embodiment of the patella knee joint bandage with a U-shaped pressure pad and with 2 pressure pad centering clasp laterally disposed from the same.
Figure 6:
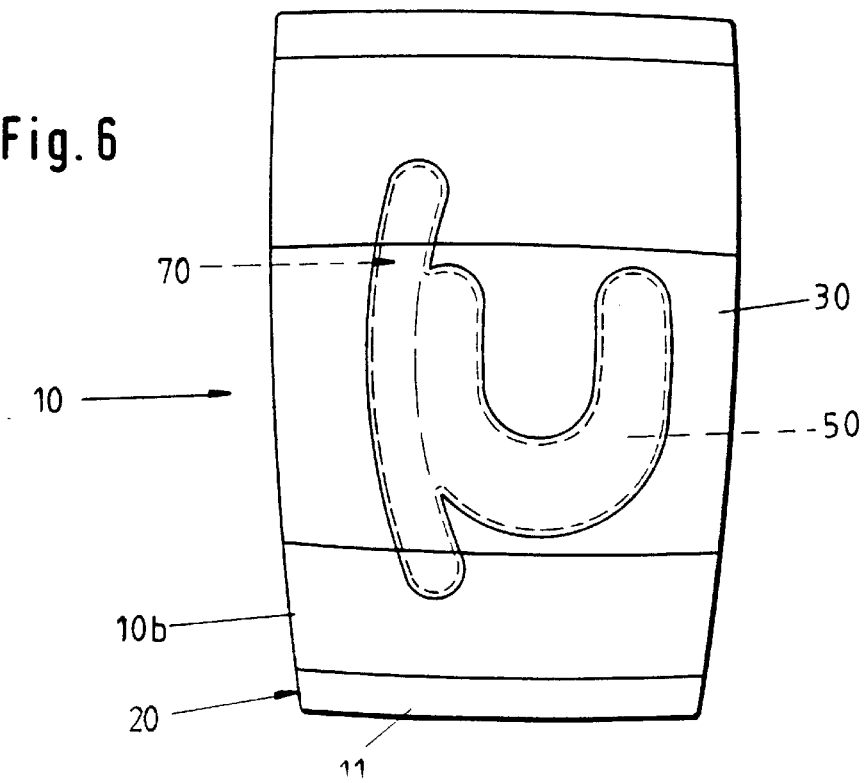
FIG. 6 shows, in a view from the front, a further embodiment of the patella knee joint bandage with a U-shaped pressure pad and with a pressure pad centering clasp integrated into one of the pressure pad legs of the same.

The pressure pad stabilization clasp 70 is located adjacent to one of the two legs 51,52 of the pressure pad 50. In its design, the clasp 70 corresponds to the shape of the external leg border 50a or 50b of the pressure pad 50 (FIG. 3). The clasp 70 can be disposed at a distance from the leg 51 of the pressure pad 50. Between the leg 51 of the pressure pad 50 and the clasp 70, a woven or a knitted fabric section 41 is then disposed (FIG. 3). However, the possibility also exists of disposing the clasp 70 without any distance beside the leg 51 of the pressure pad 50 (FIG. 5). In a further embodiment, the clasp 70 is formed onto the leg 51 of the pressure pad 50 and consequently is an integral part of the pressure pad 50 (FIG. 6). The clasp 70 and the pressure pad 50 are then constructed in one piece, while the clasp 70 possesses a dimensional elasticity corresponding to its effect.

Figure 8:
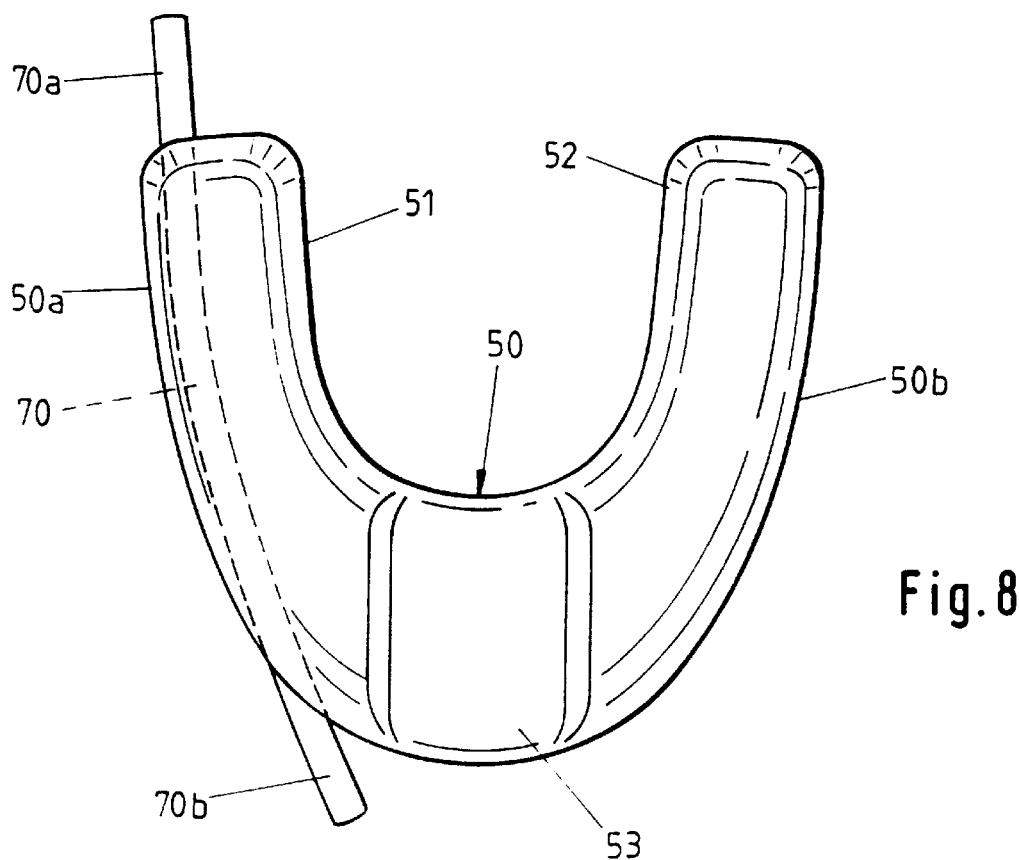
FIG. 8 shows, in a view from the front, the U-shaped pressure pad with a pressure pad centering clasp formed onto one of the pressure pad legs.

According to FIG. 7, the clasp 70 is passed through the leg 51 of the pressure pad 50 and embedded in the pressure pad material. In the embodiment shown in FIG. 8, the clasp 70 is embedded in the leg 51 of the pressure pad 50 and this in such a way that the clasp 70 projects at both ends from the pressure plate leg 51 with one section 70a, 70b each.

The pressure pad stabilization clasp 70 is preferably comprised of a springable elastic material so as to be able to adapt to all coordinated movements. By preference the clasp 70 is comprised of a plastic possessing an adequate elasticity and a degree of hardness which is higher than the degree of hardness of the material of which the pressure pad 50 is comprised. In the longitudinal direction, the clasp 70 is inelastic, but it can also be elastic in the longitudinal direction.

Figure 9:
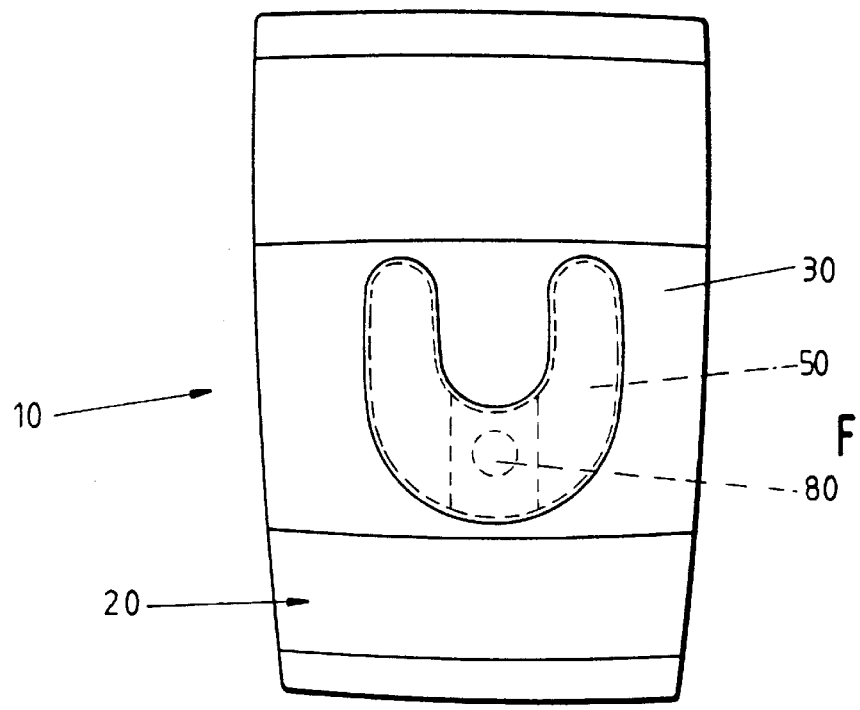
FIG. 9 shows, in a view from the front, a genu knee joint bandage with a U-shaped pressure pad provided with a friction core.

A button-like friction core 80 is incorporated into the pressure pad 50 which is comprised of a material which, in comparison with the degree of hardness of the pressure pad material, possesses a higher degree of hardness. This friction core 80 is axially disposed in the web 53 of the pressure pad 50 which interconnects the two legs 51,52 (FIGS. 9 and 10). The difference between the hardness of the pressure pad 50 and the hardness of the friction core 80 is at least 10 Shore A, preferably though 20 Shore A. The material of the pressure pad 50 may also have a hardness below 50 Shore A and the material of the friction core 80, a hardness of above 50 Shore A. What is essential is that the friction core 80 is comprised of a material which is somewhat harder in comparison with the material of the pressure pad 50.

While the pressure pad 50 is comprised of a soft or soft-elastic material, preferably of a viscoelastic silicone rubber or an elastic, compressible, pressure-deformable silicone rubber, e.g. having a hardness of 40 Shore A, a silicone rubber having a hardness of from 9 through 13 Shore A or of a compressible, pressure-deformable silicone rubber which is restored in its form without any resilience of the type of a cold caoutchouc which vulcanizes according to the method of polyaddition, which, apart from a high flexibility, possesses a hardness of below 4 Shore A, it being also possible, however, for silicone rubber to be employed in this case whose hardness lies above 4 Shore A, the friction core 80 is comprised of a hard and incompressible plastic. Such viscoelastic silicone rubbers or materials possessing the same elasticity properties employed for the fabrication of the pressure pad 50 have the property of acting massagingly when a bandage with such a pressure pad 50 is applied on account of the gliding movement triggered by mass displacement when pressure is applied or in coordinated movements. For the fabrication of the pressure pad 50, a material should at all times be selected which is viscoelastic and, owing to its elastic qualities, effects a massage.

In comparison with the pressure pad 50, the friction core 80 is comprised of a hard or incompressible plastic possessing a degree of hardness of e.g. above 50 Shore A and which consequently has a by far greater hardness than the pressure pad 50, so as to achieve, in a movement, a specific friction massage on special painful points of the joint. As material for the friction core 80, natural or synthetic rubber or hard rubber can be employed. It is thus possible, inter alia, to use a chloroprene polymerisate (commercial name NEOPREN) having a hardness of 50 Shore A, a rubber-elastic, cross-linked polyurethane (commercial name VULKOLLAN) having a hardness of from 65 through 90 Shore A, a silicone rubber having a hardness of 60 Shore A, an ethylene-proylene-diene caoutchouc (EPDM) having a hardness of 80 Shore A or a copolymerisate with acrylonitrile (commercial name PERBUNAN) having a hardness of 70 Shore A abd, further, a polyamide may be made use of. However, it is also possible to employ other plastic materials or derivatives of natural substances for the manufacture of the friction core. What is essential is that the friction core 80 possesses an adequate hardness in order to be able to exert the selective friction massage on special painful points. The friction core 80 may also be comprised of metal or wood.

The friction core 80 may be disposed in the pressure pad 50 so as to be interchangeable. For this the pressure pad 50 is provided with a recess not shown in the drawing which has approximately the size of the friction core 80, into which the friction core 80 is pressed by means of a slight pressure. The inner wall surface delimiting the recess in the pressure pad 50 preferably possesses a design which makes an engagement into the contour of the circumferential wall area of the friction core 80 possible and, since the material of the pressure pad 50 is elastic but the friction core 80 is of a greater hardness than the pressure pad material, the friction core 80 allows itself to be pressed into the recess, in which case, during the pressing operation, the contour of the inner wall area is compressed in such a way that the friction core 80 is able to glide completely into the recess and, on account of the elastic recovery capability of the material of the pressure pad 50, the pressure pad material is pressed into the marginal contour of the friction core 80 so that the same is firmly retained in the pressure pad 50. By a pertinent deformation of the pressure pad 50 due to a strong external application of pressure, the friction core 80 can be pressed out of the pressure pad 50. The possibility is provided thereby of it being possible to use friction cores possessing different degrees of hardness. In the case where pressure pads 50 having interchangeable friction cores 80 are employed, the pressure pad 50 is attached to the tubular body 20 of the bandage 10 in such a way that a removal of the pressure pad 50 is possible.

The friction core 80 according to FIG. 28 possessing a circular, square, rectangular cross-section or a cross-section having some other geometric configuration, is, within the region of its circumferential wall area 81, provided with a constriction in the form of a channel 82, groove-like recesses, undercuts, denticulations or the like which serve for the accommodation of the pressure pad material so that the friction core 80 is fixed in its position in the shaped member of the pressure pad 50. By preference the disposition of the friction core 80 in the pressure pad 50 is arranged in such a way that the same comes to be located closely underneath the surface of the pressure pad 50 in order to thus be able to exert a strong pressure on the joint.

The friction core 80 comprised of a hard or incompressible material is fixed in its position in the material of the pressure pad 50. The friction core 80 possesses a culotte-shaped surface 83 or has a surface design which, in construction and configuration, corresponds to the surface construction of the pressure pad 50 within the disposition area of the friction core 80.

According to a further embodiment, the material of the friction core 80 comprised of a plastic, e.g. silicone rubber, is fused with the material of the pressure pad 50 and undetachably connected with its shaped member. The friction core 80 may also be obtained during the fabrication of the pressure pad 50 by curing the material of a section which is to form the later friction core and, for this reason, possesses a greater hardness in comparison with the soft material of the pressure pad 50. In both cases, silicone rubber should preferably be used as material.

The pressure pad 50 can also be constructed so as to be pouch-like. This pouch is in that case comprised of soft-elastic plastics. The interior of the pouch is fitted with a gaseous medium, e.g. air, or with a liquid medium, such as e.g. viscous silicone oil, water or the like. The friction core 80 is then fixed in its position on the inner wall area of the pouch.

The genu knee joint bandage 10a is provided with a friction core 80 disposed in its pressure pad 50 as described above (FIGS. 1 and 2), whereas the patella knee joint bandage 10b is provided with the pressure pad 50 which can be constructed with or without friction core 80 (FIGS. 3 and 4). The function of the pad 50 is that of a pressure pad.

Figure 20:
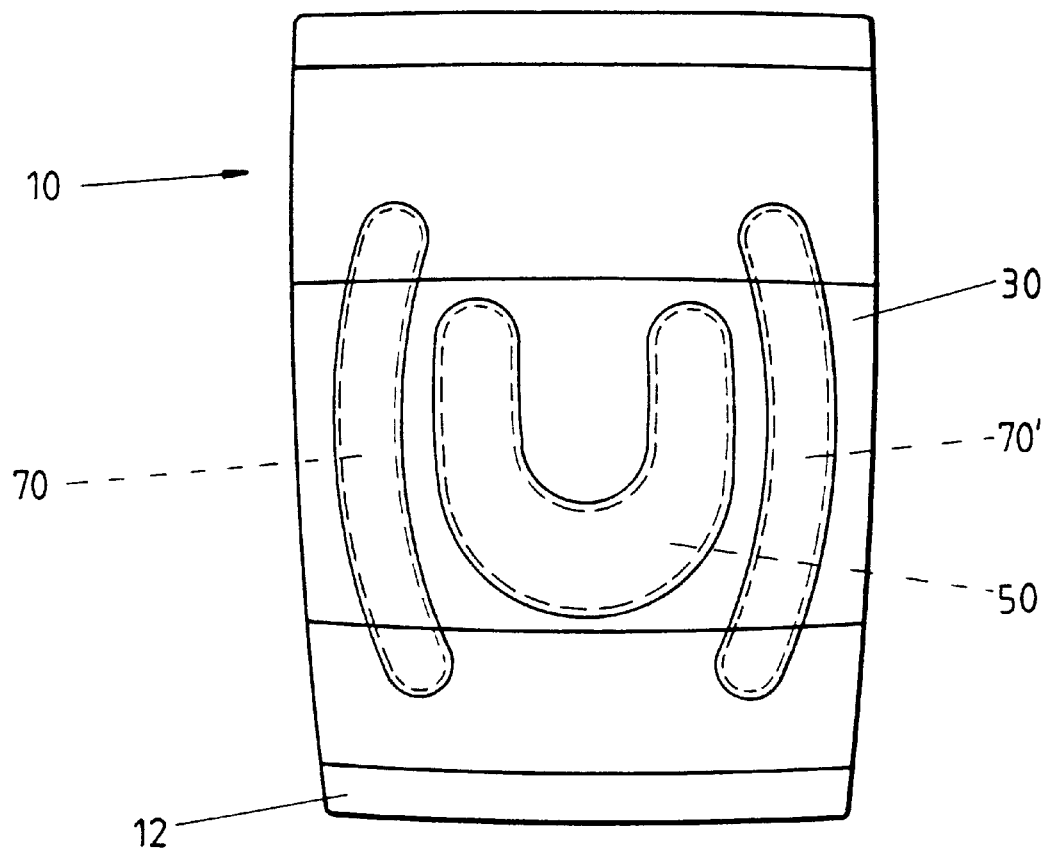
FIG. 20 shows, in a view from the front, a patella knee joint bandage with a U-shaped pressure pad and with two pressure pad centering clasps disposed laterally to the same.

In the embodiment depicted in the FIGS. 3 and 4, a pressure pad stabilization clasp 70 is disposed laterally to the pressure pad 50. However, the possibility also exists of disposing, in the front bandage portion 12 at both sides of the legs 51,52 of the pressure pad 50, one stabilization clasp 70, 70' each (FIG. 20).

The pressure pads 60,60' sewn into the rearward bandage portion 111 according to a further embodiment are comprised of the same material as the pressure pad 50. Apart from an elliptic construction, the pressure pads 60,60' may also possess a different configuration. Each of these two pressure pads 60, 60' is constructed in the form of a bead-like body. In lieu of two pressure pads 60,60', it is also possible for only one pressure pad 60 or 60' to be sewn into the rearward bandage portion 11.

Figure 16:
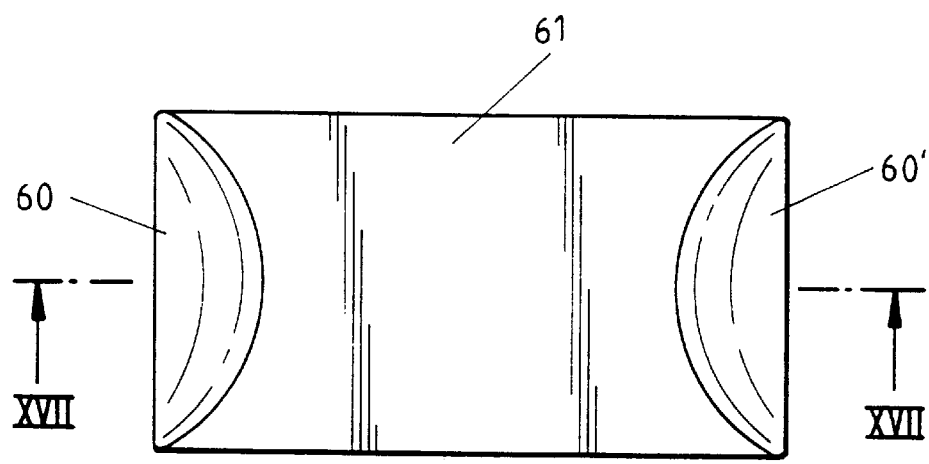
FIG. 16 shows, in a view from the front, two elliptic pressure pads interconnected by a web.
Figure 17:
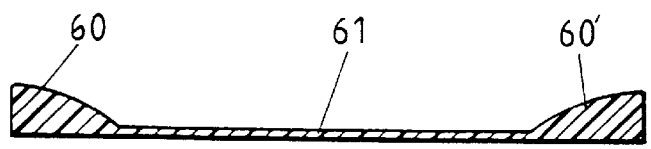
FIG. 17 shows a vertical section in the direction of line XVII—XVII in FIG. 16.

The two pressure pads 60,60' in the rearward bandage portion 11 can be interconnected by means of a web 61 (FIGS. 16 and 17). Over and above that, the possibility also exists of connecting the two pressure pads 60,60' in the rearward bandage portion 11 with the aid of webs 58,59 with the legs 51,52 of the pressure pad 50 (FIGS. 18 and 19). The webs 61 and 58, 59 connecting the pressure pads 60,60' with each other or with the pressure pad 50 are constructed so as to be thin-walled and are comprised of the same material as the pressure pads 60,60' so that these webs 61 and 58,59 possess a high degree of flexibility.

The rearward bandage portion 11 is sewn in together with the pretensioned wavy knitted fabric 40 (FIGS. 1 and 2). The pressure pad 50 as well as the pressure pads 60,60' and the pressure pad stabilization clasp 70 are disposed in the region of the insert 30 of the wavy knitted fabric 40 integrated into the tubular body 20 of the bandage 10.

In the front bandage portion 12, the wavy knitted fabric 40 of the insert 30 has a larger number of waves 42 than in the rearward bandage portion 11. The guiding of the waves 42 of the wavy knitted fabric 40 of the insert 30 starts out from a smaller number of waves in the rearward bandage portion 11 to a division of the waves 42 into two groups of waves 46, 46' proceeding at a distance from each other in the front bandage portion 12, while in the interspace 45 formed between the two groups of waves 46,46' in the front bandage portion 12, a wave group 46" that runs out into wedge-shaped terminal sections 47,47' is disposed (FIGS. 21 and 22). When sewing the front bandage portion 12 together with the rearward bandage portion 11, the wavy knitted fabric is elongated with the smaller number of waves 42 while the wavy knitted fabric in the front bandage portion 12 is simultaneously contracted (FIG. 23). A peculiarity of the bandage 10 consists in that, for the insert 30 which is provided where the greatest alternating elongation stresses of the bandage occur, a special textile structure is employed, viz. the wavy knitted fabric 40, which will be explained in greater detail hereinafter. However, the possibility also exists of letting the waves 42 of the wavy knitted fabric 40 of the insert 30 in the front bandage portion 12 proceed linearily and parallelly.

Figure 24:
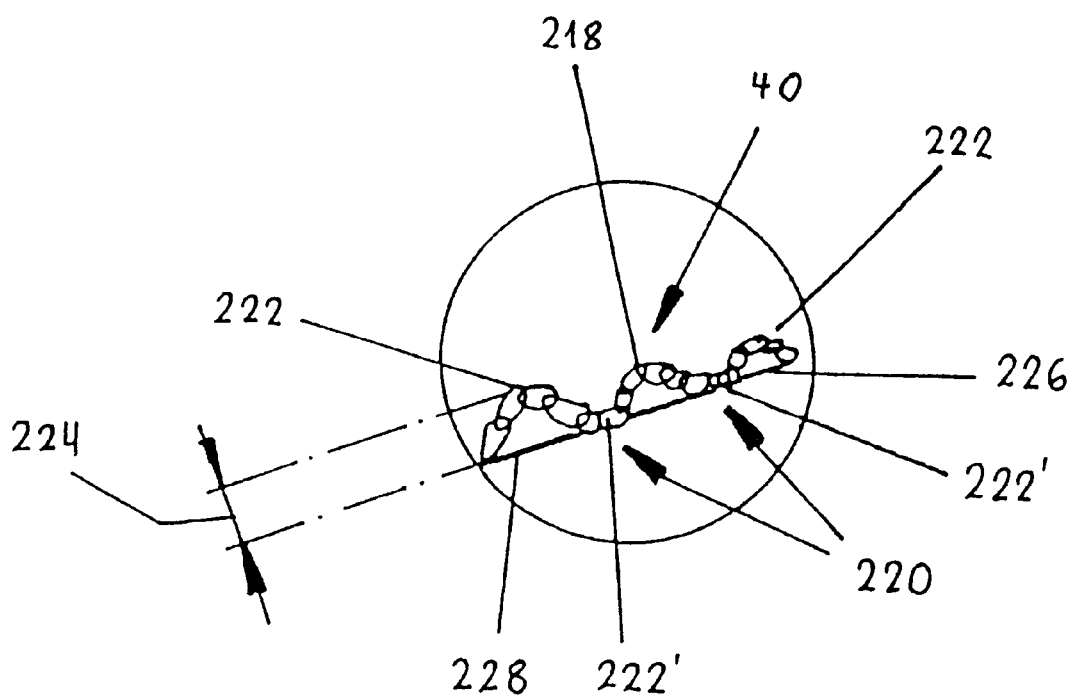
FIG. 24 shows an enlarged section through the insert of the wavy knitted fabric in the direction of Line XXIV—XXIV in FIG. 23.

The strip-like reproduction of the insert 30 in the FIGS. 21 and 22 indicates that the wavy knitted fabric 40 forms a relief within this region, which is shown more distinctly in the representation according to FIG. 24. This relief is a wave structure which is formed on at least one side of the bandage—in the embodiments shown in the drawings, on the side facing away from the body. On this occasion, a series of half-waves 218 is strung together with the interposition of notched points or zones 220, which are formed as detailed in the following.

A knitted covering fabric 224 formed of meshes 222 is, within the area of individual meshes 222', firmly connected with an elastic thread arrangement 226 on the underside of the knitted covering structure 224 in such a way that a course of meshes 222 of the knitted covering fabric 224—in the embodiment, four—is bridged by a longer mesh 228 of the subjacent, elastic thread arrangement 226. The meshes 222 between the notched points or zones 220 are made to bulge out upwardly thereby, whereby the transverse waves 218 are pretensioned and stabilized. It is possible to selectively influence the deformational behavior and the permanent elasticity by varying the number of bridged meshes 222 and/or the meshes 228.

Figure 25:
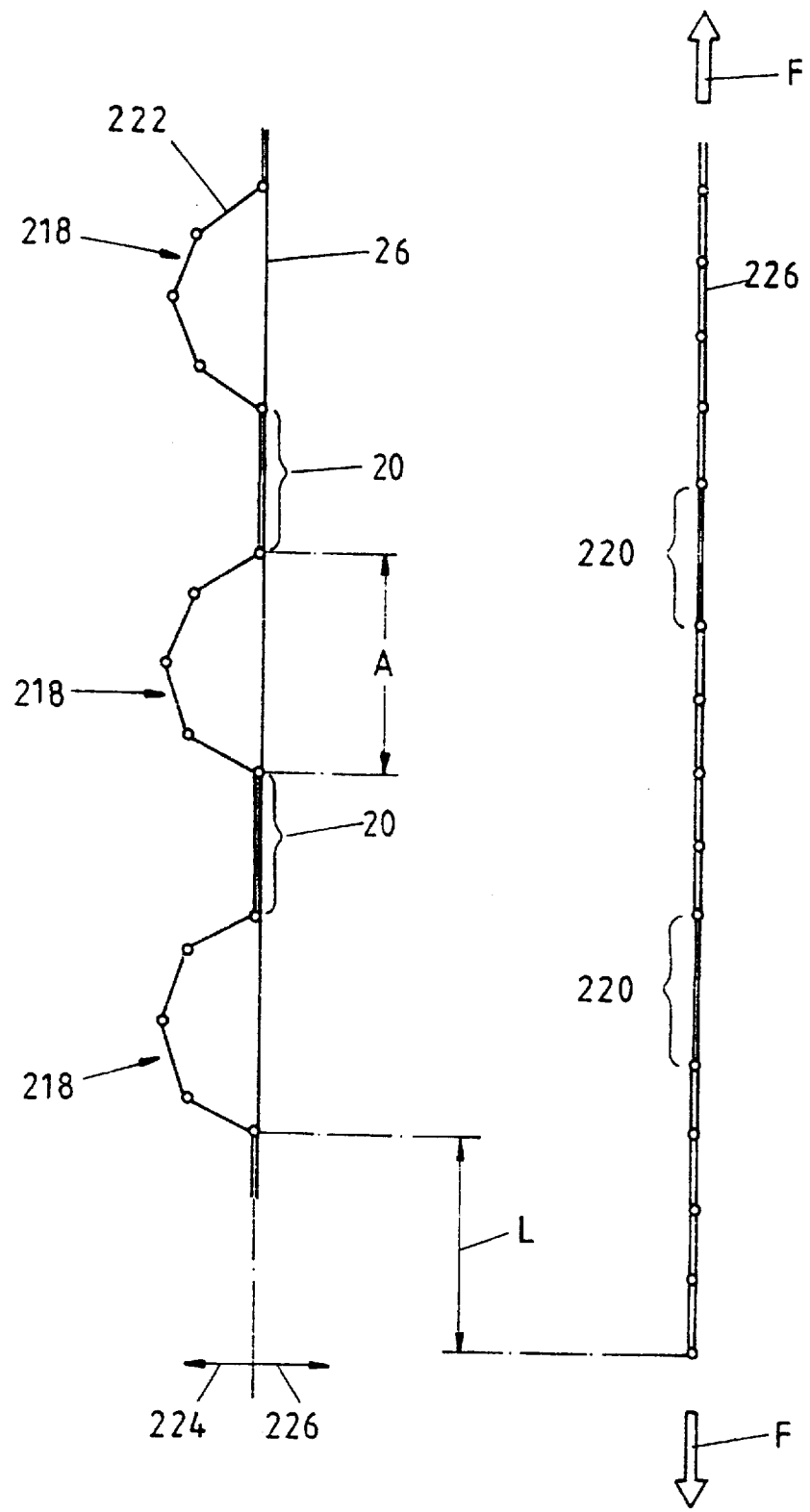
FIG. 25 shows, in a schematic simplified representation, the principle of the deformation of a fabric comprised of the wavy knitted fabric.

The deformational bahavior of the wavy knitted fabric 40 formed in this way becomes apparent in detail from the representation according to FIG. 25. On the left-hand side the wavy knitted fabric is shown in the relieved state. The meshes are indicated by means of lines and the connection of the meshes with each other by means of small circles.

The elastic yarn 226 provided on the underside bridges the nodal zones 220, between which four meshes 222 of the knitted covering fabric 224 are constructed at a time.

By means of the pretension of the elastic thread arrangement 226, the meshes 222 are caused to bulge out in the form of half-waves 218, whereby the relief structure is formed. The half-waves 218 possess in each case between two and twelve, preferably though, four, courses of meshes.

On the right-hand side it is illustrated how the wavy knitted fabric 40 behaves when strained by a tensile force F. It is visible that the elastic thread arrangement 226 is elongated between the nodal zones 220 without that an additional elongation stress occurs in the region of the half-waves 218, i.e. within the region of the meshes 222. Accordingly the wavy knitted fabric 40 is capable of being lengthened by the dimension L prior to the meshes 222 of the knitted covering fabric 224 being strained by tension. This dimension L accordingly provides an elongation reserve of the knitted bandage fabric in comparison with conventional textile fabrics.

The connection between the knitted covering fabric 224 and the elastic thread arrangement 226 may be established in the most widely varying ways. It is also possible to select or establish the connection in such a way that waves 42 are formed on both sides of the wavy knitted fabric 40. The knitted covering fabric 224 does not need to be single-faced in its construction.

Owing to the projecting structure of the wavy knitted fabric 40, it is possible, in spite of a high degree of elongation for the knitted covering fabric, to employ normal knitting yarn, such as e.g. cotton or polyamide yarn. For the elastic thread arrangement 226, preferably higher elastic yarn, such as e.g. covered yarn, is used, in which connection it is possible for this elastic thread to be additionally plaited in order to improve the wear resistance of the textile fabric or knitted fabric.

Furthermore, a laid-in yarn can be incorporated into the meshes 222 of the knitted covering fabric 224 in order to achieve also in this region of the wavy relief structure a compressive effect of the bandage.

Figure 26:
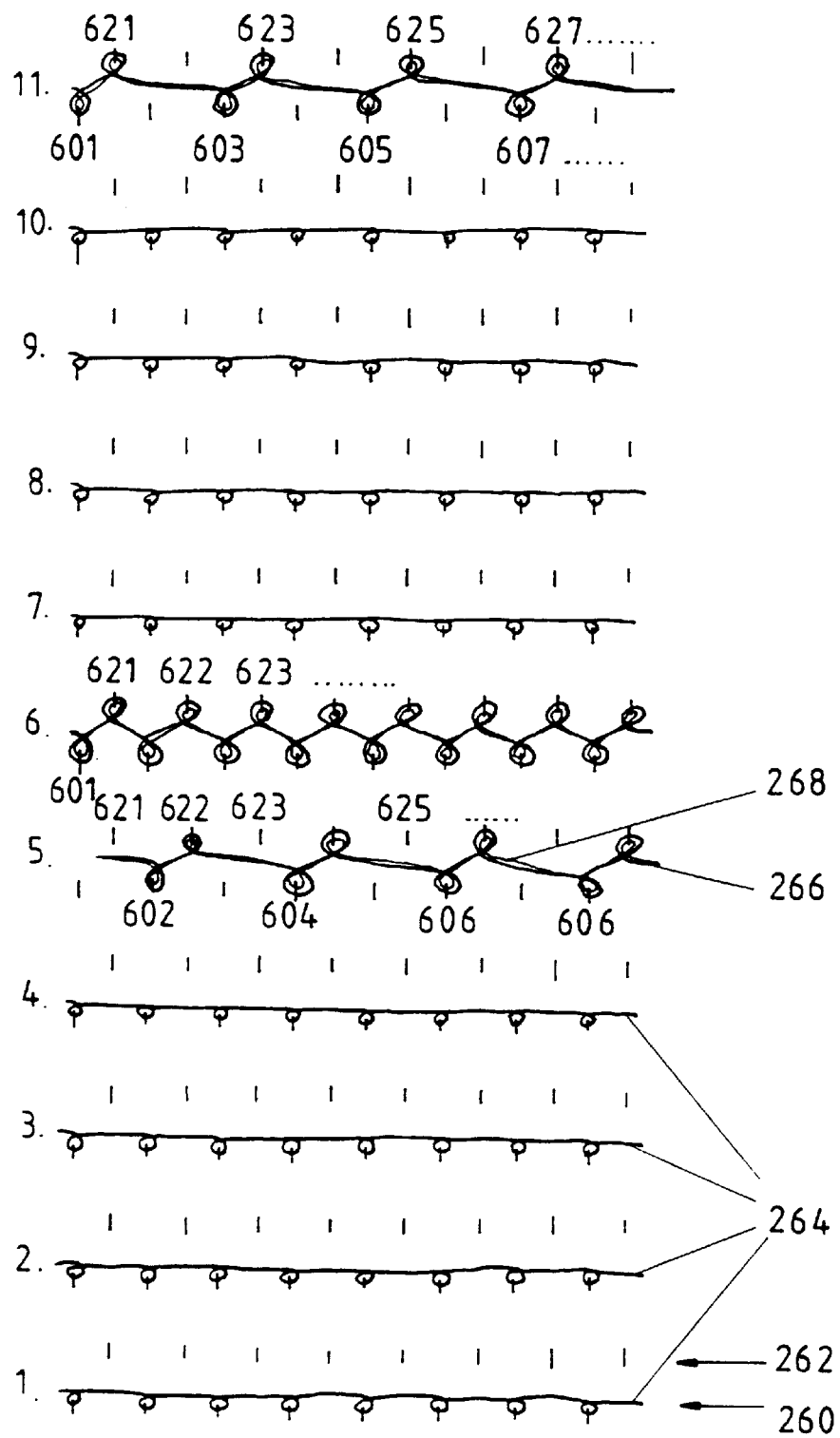
FIG. 26 shows representations of knitting courses for clarifying a first embodiment of a method for producing the wavy knitted fabric.
Figure 27:
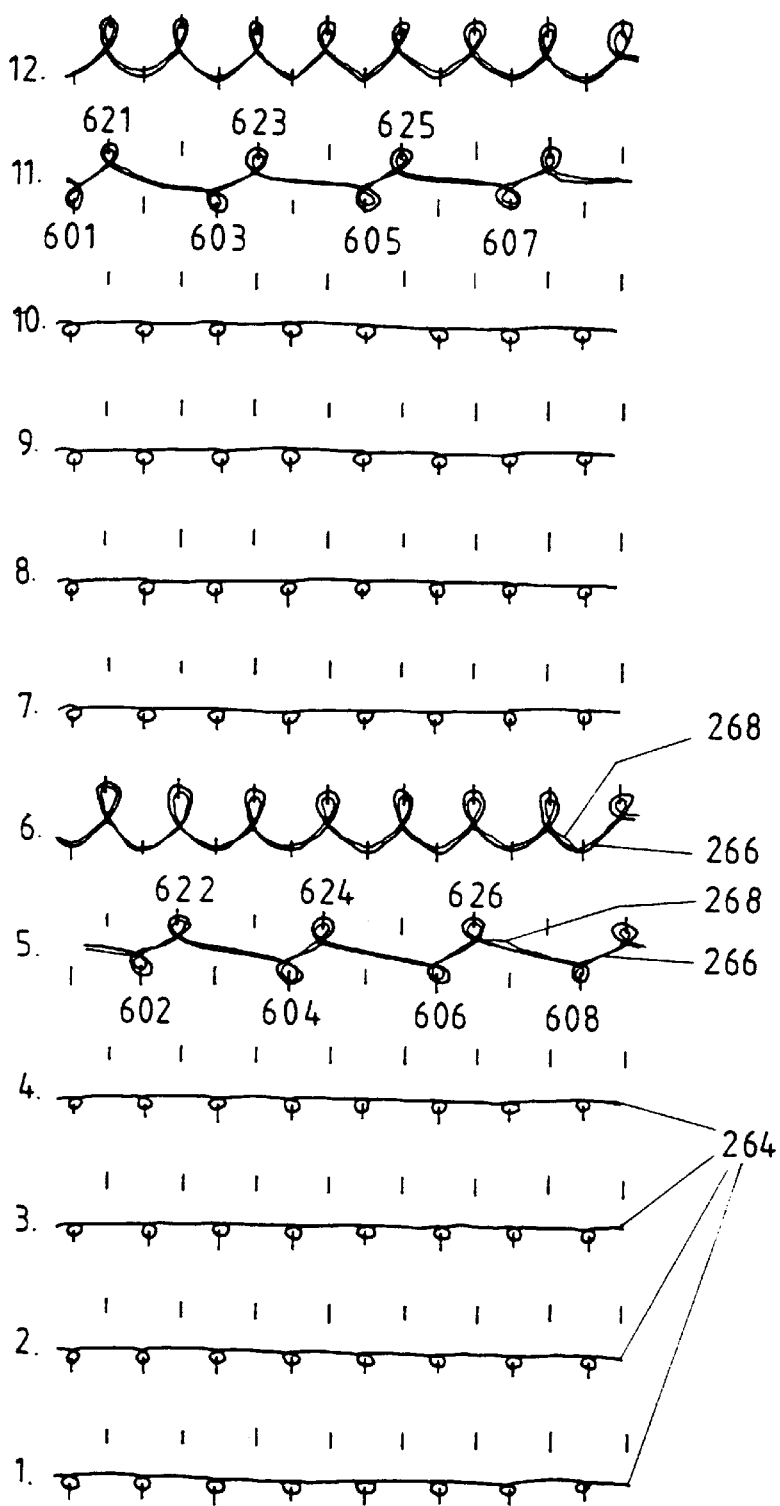
FIG. 27 shows, in a representation resembling the FIG. 26, a further knitting design for the wavy knitted fabric.

Two possibilities are shown in the FIGS. 26 and 27 of how the wavy knitted fabric 40 explained in the foregoing can be produced on automatic knitting machines. On this occasion two needle beds are employed, viz. a first needle bed 260 and a second needle bed 262 with needles disposed at an indentical distance from each other. On the first needle bed 260, several—in the embodiment example shown, four—courses a meshes of normal knitting yarn, such as e.g. cotton or polyamide yarn 264, are knitted. Following this, two courses of meshes are knitted on both needle beds 260,262 with elastic yarn, such as e.g. rubber or covered yarn 268, in which case a plaiting thread 266 is preferably added to this elastic yarn. In the fifth knitting course, knitting is carried out only on selected needles 602,604,606, . . . , etc., or 622,624,626, . . . , etc., of both needle beds. The plaiting thread may be a highly elastic polyamide thread. The illustration shows that the course six is again knitted on all the needles of the two needle beds 260,262. However, this is no absolute necessity.

Then, once more follow four courses with ordinary yarn on the first needle bed 260 and, finally, two further courses in which elastic yarn is employed, in which case the eleventh knitting course differs from the fifth knitting course in that the participating needles of the needle beds 260,262 are offset by one.

FIG. 27 depicts another knit design having a somewhat different knitting construction within the region of the later knitted fabric knots 220. The knitting courses one through five and seven through eleven correspond to the knit pattern according to FIG. 26. Different is merely the formation of the sixth and the twelfth knitting courses, so that it does not appear necessary to go into this figure in greater detail.

In a departure from the previously described manufacturing method it is also possible to first knit on a needle bed one or several courses of elastic yarn, such as e.g. covering yarn and, on the other needle beds, courses of normal knitting yarn, such as e.g. cotton or polyamide yarn, in which connection subsequently one or more courses are knitted with all the needles or individual needles of both needle beds.

No restriction exists to the effect that the insert 30 is comprised of a wavy knitted fabric 40 described in the foregoing. What is decisive is merely that the textile fabric forming the insert (30) receives such a construction that either an incorporated elastic thread arrangement or an elastic thread arrangement connected with a covering textile structure in conformity with a predetermined pattern or design imparts such an internal pretension to the fabric that, at least on one side, a wavy relief is formed that, by means of an external stress, can then first be pulled smooth or smoother without already in this phase straining the covering structure by elongation.

The insert 30 of the wavy knitted fabric 40 prevents a creasing or counteracts a creasing, especially within the internal flexing region of the applied bandage 10.

By preference the pressure pad stabilization clasp 70 is passed out at both ends from the insert 30 of the wavy knitted fabric 40, in which case the free clasp ends are sewn into the woven or knitted fabric of the tubular body 20 of the bandage 10.

In order to obtain an almost continuous transition to the bandage from the pressure pad 50, the web of the pressure pad 50 can be provided with a tongue-like formed-on portion running out taperingly to the outer border, which is comprised of the material of the pressure pad. The possibility also exists of allowing the outer marginal area of the web to run out taperingly in its web sections located on both sides of the web center. The external border of the pressure pad web is thus constructed so as to be running out flat toward the outside. The free ends of the legs of the pressure pad can be constructed so as to be broadened in the manner of an elephant foot, whereby the bearing region and action area of the pressure pad 50 is improved.

Figure 31:
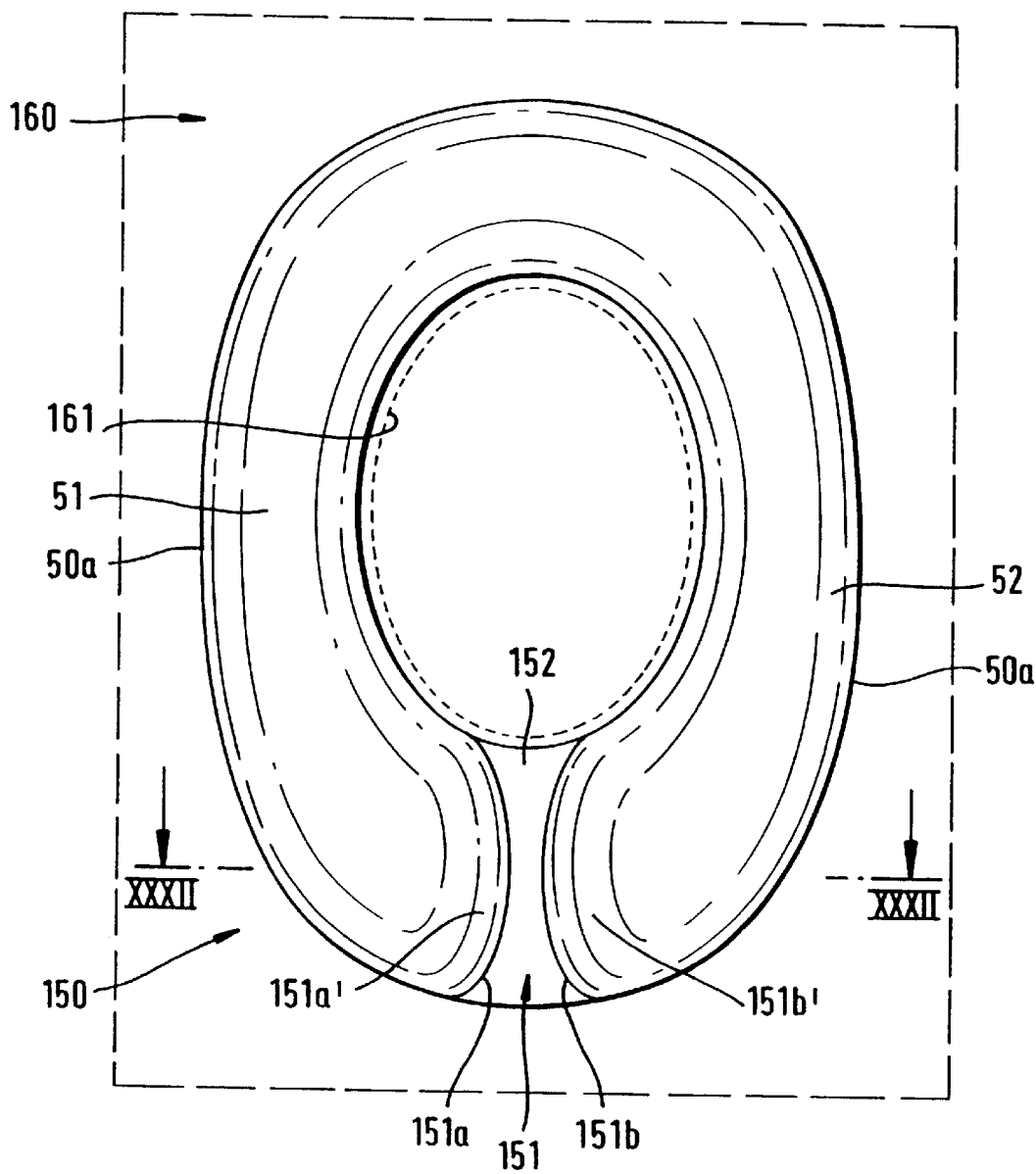
FIG. 31 shows, in a view from the top, an annular pressure pad.
Figure 32:
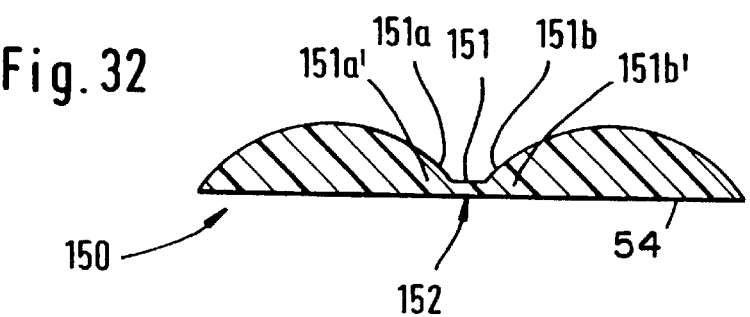
FIG. 32 shows a vertical section in the direction of Line XXXII—XXXII in FIG. 31.
Figure 33:
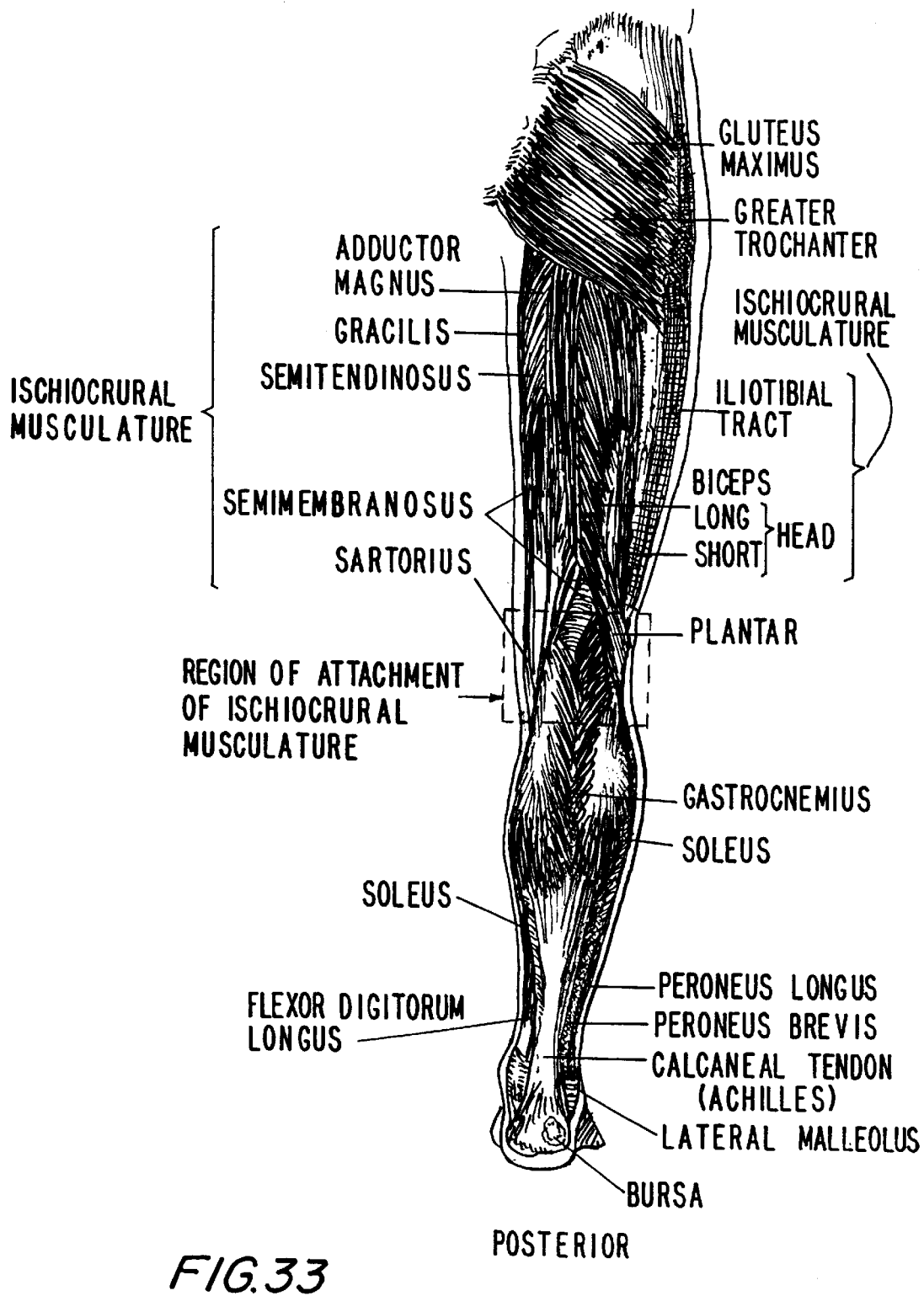
FIG. 33 shows the right lower extremity illustrating the location of the attachment of the ischiocrual musculature.

According to a second embodiment, the pressure pad 150 disposed in the front bandage portion 12 is constructed so as to be annular and preferably possesses an oval configuration or the form of an ellipse. Within the lower region, the two pressure pad legs 51,52 pass into a narrow, thin-walled pressure pad section 152 in the form of a web-like depression 151, in which case the lateral rims 151a, 151b which delimit the web-like depression 151 proceed, as depicted in FIG. 31, linearly or in the form of a circular arc, whereby a lateral friction on both sides of the tendon attachment is achieved. This friction is additionally aided in that, within the region of the section 151a', 151b' of the pressure pad legs 51,52 terminating in the region of the lateral rims 151a, 151b, possess a bead-like configuration (FIG. 32). The pressure pad 150 is comprised of the same materials as the pressure pad 50, the attachment of the pressure pad 150 to the front bandage portion 12 is effected with the aid of a fabric section 160 fitted on the inside and comprised of a thin material so that a double-walled construction is obtained. In the thusly constructed interspace, the pressure pad 150, which is retained in an immovable position with the aid of a seam identified with 161, which connects the blank 160 with the fabric of the bandage portion 12 (FIG. 31).

What is claimed is:

1. A bandage for the knee joint of elastic bandage cloth in tubular form with a front bandage portion (12) and a rear bandage portion (11) and with at least one inserted, longitudinally proceeding spring rod, the bandage (10a) being comprised of an anatomically configured tubular body (20) of a woven or knitted fabric and in the front bandage portion (12), a padding (50) fabricated from a soft material having two padding legs (51, 52) being disposed so as to be located within the region over the patella when the bandage (10a) is applied, the padding (50) being open toward the top and adapted to leave the quadriceps tendon uncovered, wherein the woven or knitted fabric of the bandage (10*a*) is comprised of a fully circumferential gusset (30) of a highly elastic undulated knitted fabric (40), the upwardly open padding (50) possessing an arcuated course of outer rims (50*a*, 50*b*) of the two padding legs (51, 52) and a flat surface (54) as well as a semicircular or partially circular leg cross-section, the padding (50) further possessing centrally thereof a padding web (53) interconnecting the two legs of the padding (51, 52), an internally located depression (55) for adaption to the tibial condyle and to the course of the ligamentum patellae, and wherein the length of the depression (55) corresponds to the width of the padding web (53).

2. The bandage according to claim 1, wherein the undulations (42) of the wavy knitted fabric (40) of the gusset (30) proceed linearity and parallelly in the front bandage portion (12).

3. The bandage according to claim 1, wherein guiding of the undulations (42) of the wavy knitted fabric (40) of the gusset (30) is effected from a small number of undulations within the rear bandage portion (11) to a division of the undulations (42) into two undulation groups (46,46') in the front bandage portion (12) proceeding spaced apart from each other, while between the two undulation groups (46, 46') an undulation group (46') is disposed which runs out into wedge-shaped terminal sections (47,47').

4. The bandage according to claim 3, wherein, when the front bandage portion (12) is sewn together with the rear bandage portion (11), the wavy knitted fabric (40) possessing the smaller number of undulations in the rear bandage portion (11), the wavy knitted fabric in the front bandage portion (12) is gathered.

5. The bandage according to claim 1, wherein the padding is soft-elastic.

6. A bandage for the knee joint of elastic bandage cloth in tubular form with a front bandage portion (12) and a rear bandage portion (11) and with at least one inserted, longitudinally proceeding rod, the bandage (10*a*) being comprised of an anatomically configured tubular body (20) of woven or knitted fabric and, in the front bandage portion (12), an annular padding (150) fabricated from a soft material having two padding legs (51, 52) being disposed so as to be located within the region over the patella when the bandage (10*a*) is applied, wherein for the reduction of a pressure upon the patellar ligament the padding (150) is provided within a lower region thereof with a web-like depression while forming a thin-walled padding section, wherein lateral rims delimiting the web-like depression proceeds linearly, wherein the woven or knitted fabric of the bandage (10*a*) is comprised of a fully circumferential gusset (30) of a highly elastic wavy knitted fabric (40), the annular padding (150) having an arcuated course of external rims (50*a*), 50*b*) of the two padding legs (51, 52) and a flat surface (54) as well as a semicircular or partially circular leg cross-section, the padding (150) further comprising centrally thereof a web interconnecting the two padding legs (51, 52) and forming the web-like depression (151) delimited by lateral rims (151*a*, 151*b*), wherein the length of the web-like depression (151) corresponds to the width of the padding web, wherein, in order to reduce a pressure upon the patellar ligament within the lower region, the web-like depression (151) is constructed so as to form a thin-walled padding section (152), and wherein the sections (151, 152) of the padding legs (51, 52) terminating within the area of lateral rims (151*a*, 15*b*) possess a bead-shaped configuration so as to generate friction on both sides of the tendon attachment.

7. The bandage according to claim 6, wherein the padding is soft-elastic.

8. The bandage according to claim 6, wherein the lateral rim proceeds linearly.

9. The bandage according to claim 6, wherein the lateral rim proceeds in a circular arc.

10. A bandage for the knee joint of an elastic bandage cloth in tubular form with a front bandage portion (12) and a rear bandage portion (11) and with at least one inserted, longitudinally proceeding spring rod, the bandage (10*b*) being comprised of an anatomically configured tubular body (20) of a woven or knitted fabric, wherein, in a front bandage portion (12), a padding (50; 150) fabricated from a soft material is disposed which, when the bandage (10*b*) is applied, is located within the region over the patella, the padding (50; 150) being adapted to leave the quadriceps tendon uncovered and wherein the woven or knitted fabric of the bandage (10*a*) is comprised of a fully circumferential gusset (30) of a highly elastic wavy knitted fabric (40) and, within the front bandage portion (12), at least one padding stabilization clasp (70) is disposed which stabilizes the padding (50; 150) and which proceeds in the longitudinal direction of the bandage, wherein the padding stabilization clasp (70) is an integrated component of the padding (50; 150) and is located laterally to the padding (50; 150).

11. The bandage according to claim 10, wherein the padding stabilization clasp (70) is located adjacent to one of the two padding legs (51,52) of the first padding (50;150) and possess a configuration corresponding to that of the external leg rim (50*a*;50*b*).

12. The bandage according to claim 10, wherein the padding has two padding legs (51, 52), wherein the padding stabilization clasp (70) is disposed at a distance from one of the padding legs (51) of the two padding legs (51,52) of the first padding (50;150), while between the padding leg (51) of the first padding (50;150) and the padding stabilization clasp (70), a woven or knitted fabric section (41) is disposed.

13. The bandage according to claim 10, wherein the padding has two padding legs (51, 52), wherein the padding stabilization clasp (70) is disposed without an interspace next to one of the padding legs (51) of the two padding legs (51,52) of the first padding (50;150).

14. The bandage according to claim 10, wherein the padding has two padding legs (51, 52), wherein the padding stabilization clasp (70) is formed onto one of the padding legs (51) of the two padding legs (51,52) of the first padding (50;150).

15. The bandage according to claim 10, wherein the padding stabilization clasp (70) is passed through one of the two padding legs (51,52) of the first padding (50;150) and is embedded in the padding material.

16. The bandage according to claim 10, wherein the padding stabilization clasp (70) is passed through one of the two padding legs (51,52) of the first padding (50;150) and is embedded in the padding material, wherein the padding stabilization clasp (70) extends out at both ends from the padding leg (51) with a section (70*a*;70*b*).

17. The bandage according to claim 10, wherein the padded stabilization clasp (70) is constructed so as to be elastic.

18. The bandage according to claim 10, wherein the padding stabilization clasp (70) is constructed so as to be inelastic in the longitudinal direction.

19. The bandage according to claim 10, wherein the padding is soft-elastic.

20. A bandage for the knee joint of elastic bandage cloth in tubular form with a front bandage portion (12) and a rear bandage portion (11) and with at least one inserted, longitudinally proceeding spring rod, the bandage (10*a*) being comprised of an anatomically configured tubular body (20) of a woven or knitted fabric and, in the front bandage portion (12), a first padding (50:150) being disposed so as to be located over the patella when the bandage (10*a*) is applied, the first padding (50;150) being adapted to leave the quadriceps tendon uncovered, wherein the first padding is open toward the top and is fabricated from a soft material, wherein the woven or knitted fabric of the bandage (10*a*) comprises a fully circumferential gusset (30) of a highly elastic wavy knitted fabric (40) and, into the rear bandage portion (11), at least one rear padding (60, 60') fabricated from a soft material, the at least one rear padding having a bead-shaped body adapted to act upon the attachment of the ischiocrural musculature, the at least one rear padding connected to the first padding by at least one web, the at least one web configured such that the at least one rear padding is disposed to act upon the attachment of the ischiocrural musculature when said first padding is disposed over said patella.

21. The bandage according to claim 20, wherein the padding is soft-elastic.

22. A bandage for the knee joint of an elastic bandage cloth of tubular form with a front bandage portion (12) and a rear bandage portion (11) and with at least one incorporated longitudinally proceeding spring rod, the bandage (10*b*) being comprised of an anatomically configured tubular body (20) of a woven or knitted fabric with a fully circumferential gusset (30) of a highly elastic wavy knitted fabric, wherein, in the front bandage portion (12), a first padding (50; 150) fabricated from a soft material, is disposed so as to be located within the region over the patella when the bandage (19*a*) is applied, the first padding (50; 150) being adapted to leave the quadriceps tendon uncovered, wherein the padding is open toward the top, wherein the woven or knitted fabric of the bandage (10*a*) comprises a fully circumferential gusset (30) of a highly elastic wavy knitted fabric (40) and, in the front bandage portion (12), at least one padding stabilization clasp (70) is disposed which stabilizes the first padding (50; 150) and which proceeds in the longitudinal direction of the bandage, wherein the padding stabilization clasp (70) is an integrated component of the first padding (50; 150) and is located laterally to the first padding (50; 150), and wherein, into the rear bandage portion (11), at least one rear padding (60, 60') fabricated from a soft material, is inserted which acts upon the ischiocrural musculature.

23. The bandage according to claim 22, wherein the first padding (50;150) is configured in the manner of a "U" or a "V" and possesses a horseshoe-shaped configuration with a curved course of the external rims (50*a*, 50*b*) of the two padding legs (51,52) or an oval shape, wherein the first padding (50;150) possesses an externally located, even surface area (54), a semicircular or partially circular leg cross-section and wherein a web (53) interconnecting the padding legs (51,52) is centrally provided with an internally located hollow (55) possessing lateral guiding means (56, 57) proceeding in the longitudinal direction of the bandage for adaptation to the tibial condyle and to the course of the ligamentum patellae.

24. The bandage according to claim 22, wherein the first padding (50;150) contains a button-like friction core (80) which is incorporated into the padding material and which is comprised of a material which, in comparison with the degree of hardness of the padding material, possesses a higher degree of hardness.

25. The bandage according to claim 24, wherein the difference between the hardness of the first padding (50;150) and the hardness of the friction core (80) is at least 10 Shore A, preferably 20 Shore A, and wherein the material of the first padding (50;150) possesses a hardness of below 50 Shore A and the material of the friction core (80) has a hardness in excess of 50 Shore A.

26. The bandage according to claim 25, wherein the friction core (90) is obtained during the fabrication of the first padding (50;150) by material curing of a section of the first padding (50;150), and wherein the friction core (80) and the first padding (50;150) are comprised of plastic materials, more especially silicone rubbers possessing differing degrees of hardness.

27. The bandage according to claim 24, wherein the friction core (80), for a positional fixation in the friction core (80), for a positional fixation in the first padding (50;150) within the area of its circumferential wall area (81), has a groove-like recess, constriction, such as a groove, undercut, denticulation or the like (82) for the accommodation of the padding material.

28. The bandage according to claims 24, wherein the material of the friction core (80) is fused together with the material of the first padding (50;150) and is non-detachably connected with the padding material, wherein the friction core (80) and the first padding (50;150) are comprised of plastic materials, more particularly of silicone rubbers.

29. The bandage according to claim 22, wherein all the paddings (50;150;60,60') are comprised of felt, cellular rubber, neoprene, rubber, viscous silicone rubber or an elastic, compressible silicone rubber that is deformable by means of pressure or of a material possessing identical elastic properties, such as natural rubber.

30. The bandage according to claim 22, wherein the friction core (80) is comprised of a non-compressible plastic such as a natural or synthetic rubber, hard rubber, chloroprene polymerisate, a rubber-elastic cross-linked polyurethane, polyamide, metal, or wood.

31. The bandage according to claim 22, wherein the first padding (50;150) has a recess for accommodating the friction core (80) which is detachably retained in the recess by means of force fit or press fit.

32. The bandage according to claim 22, wherein, in the first bandage portion (12), on both sides of the padding legs (51,52) of the first padding (50;150), at least one padding stabilization clasp (70,70') is disposed.

33. The bandage according to claim 22, wherein the two paddings (60,60') in the rear bandage portion (11) are interconnected by means of a padding web (61), web and wherein the two paddings (60,60') are interconnected by means of webs (58,59) with the padding legs (51,52) of the first padding (50;150).

34. The bandage according to claim 22, wherein the spring rods (13,14) possess a curved configuration.

35. The bandage according to claim 22, wherein the rear bandage portion (11) is sewn in with pretensioned knitted fabric or wavy knitted fabric (40).

36. The bandage according to claim 22, wherein the first padding (50;150), the second and third padding (60,60') and the padding stabilization clasp (70) are disposed within the area of the gusset (30) of the wavy knitted fabric (40).

37. The bandage according to claim 22, wherein the first padding (50; 150), the at least one rear padding (60, 60') and the padding stabilization clasp (70) are disposed inside pockets which are one of constructed on the bandage (10) and sewn in to the bandage (10).

38. The bandage according to claim 22, wherein the wavy knitted fabric (40) of the gusset (30) has in the front bandage portion (12) a greater number of undulations (42) than in the rear bandage portion (11).

39. The bandage according to claim 22, wherein the spring rods (13,14) are incorporated into the tubular body material above the bottom seams interconnecting the rear bandage portion (11) with the front bandage portion (12).

40. The bandage according to claim 22, wherein the padding (60;60') or paddings (60,60') are constructed so as to be semi-elliptically configured or possess some other geometrical configuration.

41. The bandage according to claim 22, wherein the paddings (60,60') are combined so as to form one padding.

42. The bandage according to claim 22, wherein the padding is soft-elastic.

43. A bandage for the knee joint of an elastic bandage cloth in tubular form with a front bandage portion (12) and a rear bandage portion (11) and with at least one inserted, longitudinally proceeding spring rod, the bandage (10b) being comprised of an anatomically configured tubular body (20) of a woven or knitted fabric, wherein, in a front bandage portion (12), a padding (50; 150) fabricated from a soft material is disposed which, when the bandage (10b) is applied, is located within the region over the patella, the padding (50; 150) being annular in configuration, wherein the woven or knitted fabric of the bandage (10a) is comprised of a fully circumferential gusset (30) of a highly elastic wavy knitted fabric (40) and, within the front bandage portion (12), at least one padding stabilization clasp (70) is disposed which stabilizes the padding (50; 150) and which proceeds in the longitudinal direction of the bandage, wherein the padding stabilization clasp (70) is an integrated component of the padding (50; 150) and is located laterally to the padding (50; 150).

44. A bandage for the knee joint of an elastic bandage cloth of tubular form with a front bandage portion (12) and a rear bandage portion (11) and with at least one incorporated longitudinally proceeding spring rod, the bandage (10b) being comprised of an anatomically configured tubular body (20) of a woven or knitted fabric with a fully circumferential gusset (30) of a highly elastic wavy knitted fabric, wherein, in the front bandage portion (12), a first padding (50; 150) fabricated from a soft material, is disposed so as to be located within the region over the patella when the bandage (19a) is applied, the first padding (50; 150) having an annular configuration, wherein the woven or knitted fabric of the bandage (10a) comprises a fully circumferential gusset (30) of a highly elastic wavy knitted fabric (40) and, in the front bandage portion (12), at least one padding stabilization clasp (70) is disposed which stabilizes the first padding (50; 150) and which proceeds in the longitudinal direction of the bandage, wherein the padding stabilization clasp (70) is an integrated component of the first padding (50; 150) and is located laterally to the first padding (50; 150), and wherein, into the rear bandage portion (11), at least one rear padding (60, 60') fabricated from a soft material, is inserted which acts upon the ischiocrural musculature.

* * * * *